United States Patent [19]

Kalk et al.

[11] 4,139,530
[45] Feb. 13, 1979

[54] BENZO-[C]-CINNOLINIUM DYESTUFFS

[75] Inventors: Walter Kalk; Karl H. Schündehütte, both of Leverkusen, Fed. Rep. of Germany

[73] Assignee: Bayer Aktiengesellschaft, Leverkusen, Fed. Rep. of Germany

[21] Appl. No.: 758,183

[22] Filed: Jan. 10, 1977

Related U.S. Application Data

[63] Continuation-in-part of Ser. No. 173,688, Aug. 20, 1971, abandoned.

[30] Foreign Application Priority Data

Aug. 21, 1970 [DE] Fed. Rep. of Germany ....... 2041689
Dec. 9, 1970 [DE] Fed. Rep. of Germany ....... 2060598

[51] Int. Cl.² ................. C07D 237/36; C07D 401/02; C07D 413/02
[52] U.S. Cl. .................................. 544/234; 592/431; 592/458; 544/115
[58] Field of Search ............... 260/242, 250 C, 240 D, 260/247.5 DP

[56] References Cited
PUBLICATIONS

Lubs, The Chemistry of Synthetic Dyes and Pigments, Reinhold, (1955), p. 112.

*Primary Examiner*—Henry R. Jiles
*Assistant Examiner*—Bernard Dentz
*Attorney, Agent, or Firm*—Plumley and Tyner

[57] ABSTRACT

Cationic dyestuffs of the general formula

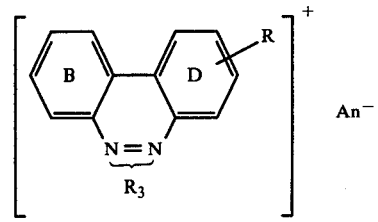

in which the symbols have the meaning mentioned above intermediates and processes for their production and their use for dyeing and printing of natural and synthetic materials.

16 Claims, No Drawings

BENZO-[C]-CINNOLINIUM DYESTUFFS

This application is a continuation in part of application Ser. No. 173,688 filed 8/20/1971 and now abandoned.

The subject-matter of the invention comprises cationic dyestuffs of the general formula

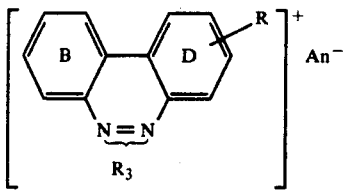

(I)

in which the rings B and D may contain further non-ionic substituents; $An^-$ means an anion; $R_3$ stands for an alkyl, aralkyl, alkenyl, alkoxy, or aralkoxy radical; R stands for $-OR_2'$, $-SR_2'$ or for

where $R_1$ stands for hydrogen, an alkyl, aralkyl, alkenyl or aryl radical, a heterocyclic radical or a group $NH_2$; $R_2$ stands for hydrogen, an alkyl, aralkyl or aryl radical, a heterocyclic radical or a group

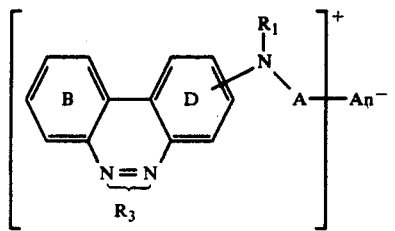

(II)

in which A means a direct bond or a bridge member, and R, $R_3$, B and D have the same meaning as above, and the radicals $R_1$ and $R_2$ may also be cyclised with the formation of a heterocyclic system; $R_2'$ means an alkyl, aralkyl or aryl radical.

Within the scope of the general formula (I), therefore, the subject-matter of the invention comprises dyestuffs of the formulae

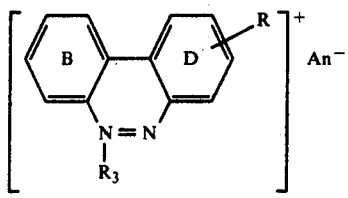

(III)

in which R, $R_3$, $An^-$, B and D have the same meaning as above, and

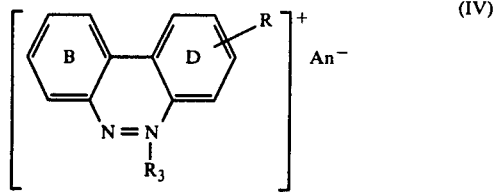

(IV)

in which R, $R_3$, $An^-$, B and D have the same meaning as above; in the case of the formula (III), the radical $R_3$ in the radical (II) stands on the left-sided nitrogen atom, and in the case of the formula (IV) the radical $R_3$ in the formula (II) stands on the right-sided nitrogen atom. 2"

Preferred dyestuffs are those of formula I, in which B is unsubstituted or substituted by anilino, methoxy, methyl, cyano, chloro, bromo, nitro, methylamino, tert.-butyl, methoxy-carbonyl, methylcarbonyl, hydroxy, sulphamoyl; except for R, D is unsubstituted or substituted by a member selected from a group consisting of chloro, bromo, methyl, methoxy, nitro and cyano; $An^{(-)}$ is an anion; $R_3$ is methyl, ethyl, n-butyl, iso-amyl, n-propyl, iso-propyl, iso-butyl, 2-methyl-propyl, pentyl, hexyl, cyclohexyl, heptyl, octyl, decyl, dodecyl, benzyl, allyl, ethoxyethyl, ethoxycarbonylmethyl, hydroxyethyl, aminocarbonylethyl, cyanoethyl or $NH_2$; R is anilino, N-methylanilino, N-ethylanilino, N-butylanilino, 2'-chloroanilino, 4'-nitroanilino, 4'-chloro-2'-nitroanilino, 2'-methylanilino, 6'-chloro-2'-methylanilino, 4'-methylanilino, 1-benzylamino, 2',4'-dimethyl-5-nitroanilino, 2',4',6'-trimethylanilino, 2'-methoxyanilino, 2'-phenoxy-anilino, 2'-acetoaminoanilino, 2',5'-diethoxyanilino, 3'-cyanoanilino, 4'-methoxycarbonylanilino, 3',4'-dicyanoanilino, 1'-aminonaphthyl, 2'-phenylethylamino, N,N-diphenylamino, methylamino, ethylamino, n-propylamino, isopropylamino, N-n-butylamino, N-cyclohexylamino, N,N-dimethylamino, N,N-diethylamino, N-methyl-N-ethylamino, morpholino, piperidino, imidazolyl, 3'-phenylpyrazolinyl-(Δ2'), 3'-(2"-ethylphenyl)-pyrazolinyl-(Δ2'), 3'-(4"-isopropylphenyl)-pyrazolinyl-(Δ2'), 3'-(4"-tert.-butylphenyl)-pyrazolinyl-(Δ2'), 3'-(4"-cyclohexylphenyl)-pyrazolinyl-(Δ2'), 3'-(4"-biphenylyl)-pyrazolinyl-(Δ2'), 3'-(4"-chlorophenyl)-pyrazolinyl-(Δ2')-, 3'-(3"-chlorophenyl)-pyrazolinyl-(Δ2'), 3'-(2"-chlorophenyl)-pyrazolinyl-(Δ2'), 3'-(2",4"-dichlorophenyl)-pyrazolinyl-(Δ2'), (3",4"-dichlorophenyl)-pyrazolinyl-(Δ2'), 3'-(4"-bromophenyl)-pyrazolinyl-(Δ2'), 3'-(3",4"-dichlorophenyl)-pyrazolinyl-(Δ2'), 3'-(4"-bromophenyl)-pyrazolinyl-(Δ2'), 3'-(4"-fluorophenyl)-pyrazolinyl-(Δ2'), 3'-(4"-acetylphenyl)-pyrazolinyl-(Δ2'), 3'-(4"-cyanophenyl)-pyrazolinyl-(Δ2'), 3'-(4"-methoxycarbonylphenyl)-pyrazolinyl-(Δ2'), 3'-(4"-methoxyphenyl)-pyrazolinyl-(Δ2'), 3'-(4"-ethoxyphenyl)-pyrazolinyl-(Δ2'), 3'-(4"-phenoxyphenyl)-pyrazolinyl-(Δ2'), 3'-(4"-isopropoxyphenyl)-pyrazolinyl (Δ2'), 3'-styryl-5'-phenyl-pyrazolinyl-(Δ2'), 3'-(4"-chlorostyryl)-5'-(4"-chlorophenyl)-pyrazolinyl-(Δ2'), 3'-(2",4"-dichlorophenyl)-pyrazolinyl-(Δ2')-, 3'-2',4"-dichlorostyryl)-5'-(2",4"-dichlorophenyl)-pyrazolinyl (Δ2')-, 3'-(2"-thienyl)-pyrazolinyl-(Δ2'), 3'-(5"-methylthienyl-2")-pyrazolinyl-(Δ2'), 3'-(2"-furyl)-pyrazolinyl-(Δ2')-, 3'-[5"-(o,p-dichlorophenyl)-furyl-2"]-pyrazolinyl-(Δ2'), 3'-(4"-pyridyl-pyrazolinyl-(Δ2'), 3'-(2"-benzoxazolyl)-pyrazolinyl-(Δ2'), 3'-(2"-benzothiazolyl)-pyrazolinyl-(Δ2'), 3'-(1"-naphthyl)-pyrazolinyl-(Δ2'), 3'-(2"-naphthyl)-pyrazolinyl-(Δ2'), 3'-phenyl-4',5'-tetramethylene-pyrazolinyl-(Δ2'), 3',4'-diphenyl-pyrazolinyl-(Δ2') or 3',5'-diphenyl-pyrazolinyl-(Δ2').

Further preferred dyestuffs are those of formula I, in which B is unsubstituted or substituted by 8-anilino, 9-anilino, 8-methoxy, 9-methoxy, 8-methyl, 9-methyl, 8-cyano, 9-cyano, 8-chloro, 9-chloro, 8-bromo, 9-bromo, 8,9-dibromo, 8-nitro, 9-nitro, 9-methylamino, 8-tert.butyl, 9-tert.-butyl, 8-methoxy-carbonyl, 9-methoxycarbonyl, 8-methylcarbonyl, 9-methylcarbonyl, 8-hydroxy, 8-sulphamoyl; except for R, D is unsubstituted or substituted by a member selected from a group consisting of 3-chloro, 3-bromo, 1-methyl, 3-methyl, 3-methoxy, 3-nitro and 3-cyano; $An^{(-)}$ is an anion; $R_3$ is methyl, ethyl, n-butyl, iso-amyl, n-propyl, iso-propyl, iso-butyl, 2-methyl-propyl, pentyl, hexyl, cyclohexyl, heptyl, octyl, decyl, dodecyl, benzyl, allyl, ethoxyethyl, ethoxycarbonylmethyl, hydroxyethyl, aminocarbonylethyl or cyanoethyl; R is 1-anilino, 2-anilino, 3-anilino, 4-anilino, 2-N-methylanilino, 2-N-ethylanilino, 2-N-butylanilino, 1-[2'-chloroanilino]-, 2-[2'-chloroanilino]-, 2-[4'-nitroanilino], 2-N-methyl-4'-nitro-anilino, 2-[4'-chloro-2'-nitroanilino]-, 2-[2'-methyl-anilino], 2-[6'-chloro-2'-methylanilino]-, 2-[4'-methylanilino]-, 1-benzylamino-, 2-benzylamino-, 3-benzylamino-, 2-N-benzyl-anilino-, 2-[2',4'-dimethyl-5-nitroanilino]-, [2',4,6'-trimethylanilino]-, 2,-[2'methoxy-anilino]-, 3-[2'-methoxyanilino-3-[2'-phenoxy-anilino], 2-[2'-acetoaminoanilino], 2-[2',5'-diethoxyanilino], 3-[2',5'-diethoxyanilino], 1-[3'-cyanoanilino], 2-[3'-cyanoanilino], 2-[4'-methoxycarbonylanilino], 2-[3',4'-dicyanoanilino], 3-[3',4'-dicyananilino], 2-[1'-aminonaphthyl], 2-[2'-phenylethylamino], 2-[N,N-diphenylamino], 1-methylamino, 2-methylamino, 3-methylamino, 2-ethylamino, 2-n-propylamino, 3-n-propylamino, 2-isopropylamino, 2-N-n-butylamino, 2-N-cyclohexylamino, 1-N,N-dimethylamino, 1-N,N-diethylamino, 2-N,N-diethylamino, 3-N,N-diethylamino, 2-N-methyl-N-ethylamino, 2-morpholino, 2-piperidino, 2-imidazolyl-, 2-[3'-phenylpyrazolinyl-(Δ2')]-, 2-[3'-(4''-methylphenyl)-pyrazolinyl-(Δ2')]-, 2-[3'-(2''-ethyl-phenyl)-pyrazolinyl-(Δ2')]-, 2-[3'-(4''-isopropylphenyl)-pyrazolinyl-(Δ2')]-, 2-[3'-(4''-tert.-butylphenyl)-pyrazolinyl-(Δ2')]-, 2-[3'-(4''-cyclohexylphenyl)-pyrazolinyl-(Δ2')]-, 2-[3'-(4''-biphenylyl)-pyrazolinyl-(Δ2')]-, 2-[3'-(4''-chlorophenyl)-pyrazolinyl-(Δ2')]-, 2-[3'-(2''-chlorophenyl)-pyrazolinyl-(Δ2')]-, 2-[3'-(2''-chlorophenyl)-pyrazolinyl-(Δ2')]-, 2-[3'-(2'',4''-dichlorophenyl)-pyrazolinyl-(Δ2')]-, 2-[3'-(3'',4''-dichlorophenyl)-pyrazolinyl-(Δ2')]-, 2-[3'-(4''-bromophenyl)-pyrazolinyl-(Δ2')]-, 2-[3'-(3'',4''-dichlorophenyl)-pyrazolinyl-(Δ2')]-, 2-[3'-(4''-bromophenyl)-pyrazolinyl-(Δ2')] 2-[3'-(4''-fluorophenyl)-pyrazolinyl-(Δ2')]-, 2-[3'-(4''-difluoromethyl)-pyrazolinyl-(Δ2')]-, 2-[3'-(4''-acetylphenyl)-pyrazolinyl-(Δ2')]-, 2-[3'-(4''-cyanophenyl)-pyrazolinyl-(Δ2')]-, 2-[3'-(4''-methoxycarbonylphenyl)-pyrazolinyl-(Δ2')]-, 2-[3'-(4''-methoxyphenyl)-pyrazolinyl-(Δ2')]-, 2-[3'-(4''-ethoxyphenyl)-pyrazolinyl-(Δ2')]-, 2-[3'-(4''-phenoxyphenyl)-pyrazolinyl-(Δ2')]-, 2-[3'-(4''-isopropoxyphenyl)-pyrazolinyl-(Δ2')]-, 2-[3'-styryl-5'-phenyl-pyrazolinyl-(Δ2')]-, 2-[3'-(4''-chlorostyryl)-5'-(4''-chlorophenyl)-pyrazolinyl-(Δ2')]-, 2-[3'-(2'',4''-dichlorophenyl)-pyrazolinyl-(Δ2')]-, 2-[3'-2',4''-dichlorostyryl)-5'-(2'',4''-dichlorophenyl)-pyrazolinyl-(Δ2')]-, 2-[3'-(2''-thienyl)-pyrazolinyl-(Δ2')]-, 2-[3'-(5''-methylthionyl-2'')-pyrazolinyl-(Δ2')]-, 2-[3'-(2''-furyl)-pyrazolinyl-(Δ2')]-, 2-[3'-[5''-(o,p-dichlorophenyl)-furyl-2'']-pyrazolinyl-(Δ2')]-, 2-[3'-(4''-pyridyl)-pyrazolinyl-(Δ2')]-, 2-[3'-(2''-benzoxazolyl)-pyrazolinyl-(Δ2°)]-, 2-[3'-(2''-benzothiazolyl)-pyrazolinyl-(Δ2')]-, 2-[3'-(1''-naphthyl)-pyrazolinyl-(Δ2')]-, 2-[3'-(2''-naphthyl)-pyrazolinyl-(Δ2')]-, 2-[3'-phenyl-4',5'-tetramethylene-pyrazolinyl-(Δ2')]-, 2-[3',4'-diphenyl-pyrazolinyl-(Δ2')]- and 2-[3',5'-diphenyl-pyrazolinyl-(Δ2')]

Further preferred dyestuffs according to the invention are those of the formula

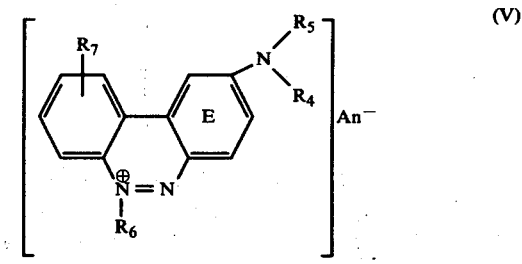

in which $R_4$ means hydrogen, alkyl with 1–4 carbon atoms or phenyl; $R_5$ means hydrogen or alkyl with 1–4 carbon atoms; $R_6$ means alkyl with 1–3 carbon atoms or benzyl; $R_7$ stands for hydrogen, halogen or alkoxy with 1–2 carbon atoms; $An^-$ means the radical of an anion; and in which the ring E may contain 1 or 2 chloro substituents.

Further preferred dyestuffs according to the invention correspond to the formula

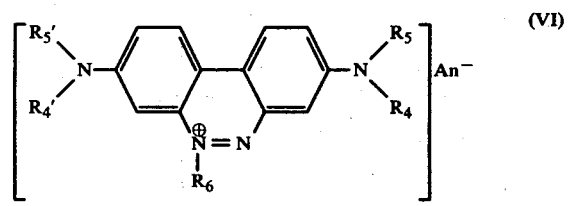

in which $R_4$, $R_5$, $R_6$ and $An^-$ have the same meaning as in formula (V); $R_4'$ means hydrogen, alkyl with 1–4 carbon atoms or phenyl; and $R_5$ represents hydrogen or alkyl with 1–4 carbon atoms or alkyl with 1–4 carbon atoms.

Dyestuffs according to the invention which are particularly preferred are those of the formula

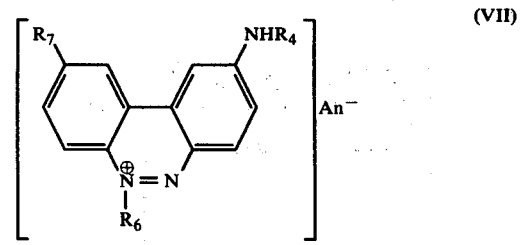

in which $R_4$, $R_6$, $R_7$ and $An^-$ have the same meaning as in formula (V), and

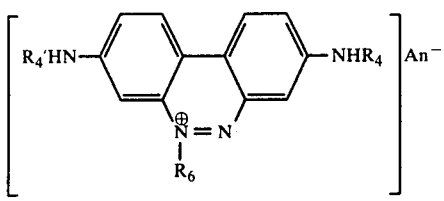

in which $R_4$, $R_4'$, $R_6$ and $An^-$ have the same meaning as in formulae (V) and (VI).

Special preference is given to dyestuffs of the formula

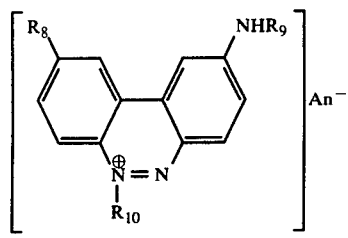

in which $R_8$ stands for Cl, Br, $-OCH_3$, $-OC_2H_5$ or H; $R_9$ stands for $-CH_3$, $-C_2H_5$ or $-C_6H_5$ (phenyl), $-C_6H_4-NH-C_6H_5$, $-C_6H_4-NH-C_6H_4-4-OCH_3$, $-C_6H_4-4-CH_3$, $-C_6H_4-4-OCH_3$ or $-C_6H_4-4-Cl$; $R_{10}$ stands for $-CH_3$, $-C_2H_5$ or $-CH_2C_6H_5$; and $An^-$ has the same meaning as above.

The subject-matter of the invention further comprises compounds of the formula

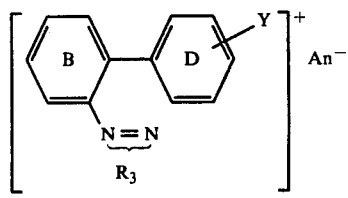

and, in particular, compounds of the formula

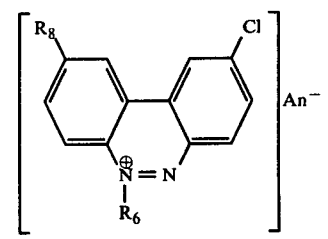

in these formulae $An^-$ means the radical of an anion; $R_3$ means an alkyl, aralkyl, alkenyl, alkoxy or aralkoxy radical; Y means a radical which can be split off; $R_6$ means alkyl with 1-3 carbon atoms or benzyl; $R_8$ means H, Cl, Br, $-OCH_3$ or $-OC_2H_5$; and the rings B and D may contain further non-ionic substituents.

The subject-matter of the invention further comprises processes for the production of dyestuffs of the formulae (I) to (IX) and processes for the preparation of compounds (X) and (XI). The invention also relates to the use of dyestuffs (I) to (IX) for the dyeing and printing of natural and synthetic materials.

By definition, the dyestuffs and compounds according to the invention may contain non-ionic substituents. Suitable substituents of this kind are, for example: fluorine, chlorine, bromine; alkyl groups, especially straight-chain or branched lower alkyl radicals with 1–6 carbon atoms; aralkyl radicals; alkenyl radicals; aryl radicals; alkoxy radicals, especially lower alkoxy radicals with 1–4 carbon atoms; aralkoxy radicals; aryloxy radicals, especially those in which aryl represents a radical of the benzene series; alkylthio radicals, preferably lower alkylthio radicals with 1–3 carbon atoms; aralkylthio radicals; arylthio radicals, preferably phenylthio and its derivatives substituted in the phenyl nucleus; nitro; cyano; alkoxycarbonyl radicals, especially those with a lower alkoxy radical of 1–4 carbon atoms; the formyl radical; alkylcarbonyl radicals, especially those with a lower alkyl group of 1–4 carbon atoms; arylcarbonyl radicals, especially those in which aryl stands for a radical of the benzene series; aralkyl-carbonyl, preferably with arylalkyl radicals the aryl nucleus of which belongs to the benzene series; alkoxycarbonyloxy radicals, preferably with lower alkoxy radicals; acylamino radicals, such as alkylcarbonylamino radicals, preferably with a lower alkyl group of 1–4 carbon atoms; aryl-carbonylamino radicals, preferably those the aryl radical of which belongs to the benzene series; alkyl-sulphonylamino radicals, preferably with a lower alkyl group of 1–3 carbon atoms; aryl-sulphonylamino groups, preferably those in which the aryl radical belongs to the benzene series; ureido, N-aryl- or N-alkyl-ureido, aryloxycarbonylamido, alkyloxy-carbonylamido; carbamoyl (carboxamide), N-alkyl-carbamoyl, N,N-dialkyl-carbamoyl, N-alkyl-N-aryl-carbamoyl; sulphamoyl, N-alkyl-sulphamoyl, N,N-dialkyl-sulphamoyl; alkyl-sulphonyl; aralkyl-sulphonyl where preferably 1–4 carbon atoms are present in the said alkyl radicals; aryl-sulphonyl radicals, especially those in which aryl stands for a radical of the benzene series; carboxylic acid alkyl ester, carboxylic acid aryl ester, sulphonic acid alkyl ester, sulphonic acid aryl ester groups.

Suitable lower alkyl radicals are primarily methyl, ethyl, n-propyl, isopropyl, n-butyl, isobutyl, tert.-butyl, iso-amyl. Substituted lower alkyl radicals which may be employed are $\beta$-chloroethyl, $\beta$-cyanoethyl, $\beta$-hydroxyethyl, $\beta$-dimethyl-aminoethyl, $\beta$-diethyl-aminoethyl, $\beta$- or $\gamma$-hydroxypropyl, $\gamma$-dimethyl-aminopropyl, $\gamma$-diethyl-aminopropyl; as well as their quaternised radicals, such as $\beta$-trimethyl-ammonium ethyl and $\gamma$-trimethyl-ammonium propyl.

Suitable cycloalkyl radicals, which may be employed are, for example cyclohexyl.

Alkyl-carbonyl stands, for example, for acetyl, n-propionyl and n-butyryl.

Aryl-carbonyl is, for example, benzoyl, 4-methyl-benzoyl, 4-chlorobenzoyl, 3-nitrobenzoyl, 4-nitrobenzoyl.

Aralkyl-carbonyl stands, for example, for benzyl-carbonyl and 4-methylbenzyl-carbonyl.

Halogen stands for fluorine, chlorine or bromine.

Lower alkoxy primarily stands for methoxy, ethoxy, n-propoxy, iso-propoxy, n-butoxy, iso-butoxy. Alkoxyalkoxy radicals which may be employed include $\beta$-methoxy-ethoxy and $\beta$-ethoxy-ethoxy.

Suitable aralkoxy radicals are, for example, benzyloxy, 2-phenyl-ethyloxy, phenylpropyl-(2,2)-oxy; and their derivatives substituted in the phenyl nucleus, such as 4-methyl-benzyloxy, 4-chloro-benzyloxy, 3-methylbenzyloxy, 2,4-dimethyl-benzyloxy and 2-methyl-4-chloro-benzyloxy.

Suitable aryloxy radicals are, for example, phenoxy and naphth-1- or -2-oxy and their derivatives substituted in the aromatic ring, such as 4-methyl-phenoxy, 2-methyl-phenoxy, 2,4-dimethyl-phenoxy and 2-methyl-4-chloro-phenoxy.

Suitable alkylthio radicals are ethylthio, ethylthio, n-propylthio and iso-propylthio.

A suitable aralkylthio radical is, for example, benzyl-thio.

Arylthio stands, for example, for phenylthio, 4-methyl-phenylthio and 4-chloro-phenylthio.

Alkoxy-carbonyl (carboxylic acid alkyl ester) radicals are, for example, methoxy-carbonyl, ethoxy-carbonyl and n-butoxy-carbonyl; aroxy-carbonyl radicals are, for example, phenoxy-carbonyl and p-methylphenoxy-carbonyl.

Alkoxy-carbonyloxy radicals are, for example, methoxy-carbonyloxy, ethoxy-carbonyloxy and n-butoxy-carbonyloxy.

Suitable alkyl-sulphonyl radicals are, for example, methyl-sulphonyl, ethyl-sulphonyl, n-propyl-sulphonyl and n-butyl-sulphonyl.

Aryl-sulphonyl groups are, for example, phenyl-sulphonyl, 4-methylphenyl-sulphonyl and 4-chlorophenyl-sulphonyl.

A suitable aralkyl-sulphonyl radical is, in particular, benzylsulphonyl.

Alkyl-carbonylamino and aryl-carbonylamino or -sulphonyl amino radicals suitable according to the invention are primarily those in which the alkyl- and aryl- carbonyl and -sulphonyl radicals correspond to those mentioned above.

Suitable anionic radicals $An^-$ are the organic and inorganic anions usual in cationic dyestuffs.

Inorganic anions are, for example, radicals of hydrohalic acids, such as fluoride, chloride, bromide and iodide anions; the perchlorate anion, the hydroxyl anion; radicals of sulphur-containing acids, such as hydrogen sulphate, sulphate, disulphate and aminosulphate anions; radicals of nitrogen-oxo acids, such as the nitrate anion; radicals of oxo acids of phosphorus, such as dihydrogen phosphate, hydrogen phosphate, phosphate and metaphosphate anions; radicals of carbonic acid, such as hydrogen carbonate and carbonate anions; further anions of oxo acids and complex acids, such as methosulphate ($CH_3OSO_2O$), ethosulphate ($C_2H_5OSO_2O$), hexafluorosilicate, cyanate, thiocyanate, hexacyanoferrate(II), hexacyanoferrate(III), trichlorozincate, tetrachlorozincate, stannate, borate, divanadate, tetravanadate, molybdate, tungstate anions; complex anions of esters of boric acid with polyhydric alcohols, such as the glycerol ester of boric acid; and also the borotetrafluoride anion.

Organic anions are, for example, radicals of saturated or unsaturated aliphatic, cycloaliphatic, aromatic and heterocyclic carboxylic acids and sulphonic acids, such as formate, acetate, α-chloroacetate, α-cyanoacetate, α-hydroxyacetate, α-aminoacetate, α-methylaminoacetate, β-aminoethyl sulphonate, β-methylaminoethyl sulphonate, n-propionate, i-propionate, n-butyrate, i-butyrate, 2,2-dimethyl acetate, 2-methyl butyrate, 2-ethyl butyrate anions; the anions of dichloroacetic acid, trichloroacetic acid, trifluoroacetic acid, 2-chloropropionic acids, 3-chloropropionic acid, 2-chlorobutyric acid, 2-hydroxypropionic acids, 3-hydroxypropionic acid, lactic acids, glycollic acid, O-ethyl glycollic acid, thioglycollic acid, glyceric acid, malic acid, dodecyl tetraethylene glycol ether-propionic acid, 3-(nonyloxy)-propionic acid, 3-(isotridecyloxy)-propionic acid, 3-(isotridecyloxy)-diethylene glycol ether-propionic acid; etherpropionic acid of the alcohol mixture with 6 to 10 carbon atoms; cyanoacetic acid, thioacetic acid, 6-benzoylamino-2-chlorocaproic acid, nonyl-phenol tetraethylene glycol etherpropionic acid, nonyl-phenol diethylene glycol etherpropionic acid, dodecyl tetraethylene glycol ether-propionic acid, phenoxy-acetic acid, nonyl-phenoxyacetic acid, n-valeric acid, i-valeric acid, 2,2,2-trimethylacetic acid, n-caproic acid, 2-ethyl-n-caproic acid, stearic acid, palmitic acid, n-pelargonic acid, lauric acid; a mixture of aliphatic carboxylic acids with 9 to 11 carbon atoms (versatic acid 911 of SHELL); a mixture of aliphatic carboxylic acids with 15-19 carbon atoms (versatic acid 1519 of SHELL); the coconut fatty acid first runnings, undecane-carboxylic acid, n-tridecane-carboxylic acid and a coconut fatty acid mixture; acrylate and methacrylate anions; as well as the anions of crotonic acid and propargylic acid; furthermore, the anionic radicals of oxalic acid, malonic acid, succinic acid, glutaric acid, adipic acid, pimelic acid, suberic acid, azelaic acid; the isomer mixture of 2,2,4- and 2,4,4-trimethyl-adipic acid; sebacic acid, isosebacic acid (isomer mixture), tartaric acid, citric acid, glyoxylic acid, galactaric acid, dimethyl-ether-α,α'-dicarboxylic acid, methylene-bis-thioglycollic acid, dimethyl-sulphide-α,α'-dicarboxylic acid, 2,2'-dithio-di-n-propionic acid, fumaric acid, maleic acid, nitrilosulphonic acid $N(SO_3H)_3$ and itaconic acid, methane-sulphonic acid, ethane-sulphonic acid, chloromethane-sulphonic acid, 2-chloroethane-sulphonic acid and 2-hydroxyethane-sulphonic acid, mersolate, i.e. $C_8$-$C_{15}$ paraffin-sulphonic acid, obtained by chlorosulphonation of paraffin oil.

Radicals of cyclic carboxylic acids are also suitable, such as the radicals of cyclohexane-carboxylic acid, cyclohexene-3-carboxylic acid; and also araliphatic monocarboxylic acids, such as phenylacetic acid, 4-methyl-phenylacetic acid, tolylic acid and mandelic acid.

Suitable anions of aromatic carboxylic acids are, for example, the radicals of benzoic acid, 2-methylbenzoic acid, 3-methylbenzoic acid, 4-methylbenzoic acid, 4-tert.-butylbenzoic acid, 2-bromobenzoic acid, 2-chlorobenzoic acid, 3-chlorobenzoic acid, 4-chlorobenzoic acid, 2,4-dichlorobenzoic acid, 2,5-dichlorobenzoic acid, 2-nitrobenzoic acid, 3-nitrobenzoic acid, 4-nitrobenzoic acid, 2-chloro-4-nitrobenzoic acid, 6-chloro-3-nitro-benzoic acid, 2,4-dinitrobenzoic acid, 3,4-dinitrobenzoic acid, 3,5-dinitrobenzoic acid, 2-hydroxybenzoic acid, 3-hydroxybenzoic acid, 4-hydroxybenzoic acid, 2-mercaptobenzoic acid, 4-nitro-3-methylbenzoic acid, 4-aminobenzoic acid, 5-nitro-2-hydroxybenzoic acid, 3-nitro-2-hydroxybenzoic acid, 4-methoxybenzoic acid, 3-nitro-4-methoxybenzoic acid, 4-chloro-3-hydroxybenzoic acid, 3-chloro-4-hydroxybenzoic acid, 5-chloro-2-hydroxy-3-methylbenzoic acid, 4-ethylmercapto-2-chlorobenzoic acid, 2-hydroxy-3-methylbenzoic acid, 6-hydroxy-3-methylbenzoic acid, 2-hydroxy-4-methylbenzoic acid, 6-hydroxy-2,4-dimethylbenzoic acid, 6-hydroxy-3-tert.-butyl-benzoic acid, phthalic acid, tetrachlorophthalic acid, 4-hydroxyphthalic acid, 4-methoxyphthalic acid, isophthalic acid, 4-chloroisophthalic acid, 5-nitro-isophthalic acid, terephthalic acid, nitroterephthalic acid, diphenylcarboxylic acid-(3,4), o-vanillic acid, 3-sulphobenzoic acid, benzene-tetracarboxylic acid-(1,2,4,5), naphthalene-tetracarboxylic acid-(1,4,5,8), biphenylcarboxylic acid-(4), abietic acid, phthalic acid-mono-n-butyl ester, terephthalic acid monomethyl ester, 3-hydroxy-5,6,7,8-tetrahydronaphthalene-carboxylic acid-(2), 2-hydroxynaphthoic acid-(1) and anthraquinone-carboxylic acid-(2).

Suitable anions are also the radicals of heterocyclic carboxylic acids, for example, the radicals of furoic acid, dehydromucic acid, indolyl-(3)-acetic acid.

Suitable anions of aromatic sulphonic acids are, for example, the radicals of benzene-sulphonic acid, benzenedisulphonic acid-(1,3), 4-chlorobenzene-sulphonic acid, 3-nitrobenzene-sulphonic acid, 6-chloro-3-nitrobenzene-sulphonic acid, toluene-sulphonic acid-(4), toluene-sulphonic acid-(2), toluene-ω-sulphonic acid, 2-chlorotoluene-sulphonic acid-(4), 1-hydroxybenzene-sulphonic acid, n-dodecylbenzene-sulphonic acid, tetrapropylenebenzene-sulphonic acid, 1,2,3-tetrahydronaphthalene-sulphonic acid-(6), naphthalene-sulphonic acid-(1), naphthalene-disulphonic acid-(1,4) or -(1,5), naphthalene-sulphonic acid-(2), naphthalene-sulphonic acid-(2,6), naphthalene-sulphonic acid-(2,7) or naphthalene-sulphonic acid-(1,3,6), naphthol-(1)-sulphonic acid-(2), 5-nitronaphthalene-sulphonic acid-(2), 8-aminonaphthalene-sulphonic acid-(1), stilbene-disulphonic acid-(2,2'), biphenylsulphonic acid-(2).

Suitable heterocyclic sulphonic acids are, for example, the radicals of quinoline-sulphonic acid-(5).

Further suitable anions are those of the following acids: nitriloacetic acid, ethylene-bis-iminoacetic acid, benzene-sulphinic acid, benzene-phosphonic acid.

Colourless or almost colourless anions are preferred. For dyeing from an aqueous solution, those anions are preferred, which do not too strongly impair the solubility of the dyestuff in water. For dyeing from an aqueous dispersion this consideration is of no importance for the selection of the anions. For dyeing from organic solvents, those anions are also frequently preferred, which further the solubility of the dyestuff in organic solvents, or at least do not adversely affect it; the anions of organic mono- and di-carboxylic acids with about 4 to 30 carbon atoms are to be mentioned in the first place.

Suitable bridge members A are the following, in particular: straight-chain or branched alkylene groups, cycloalkylene groups, aralkylene groups, arylene groups, for example the following:

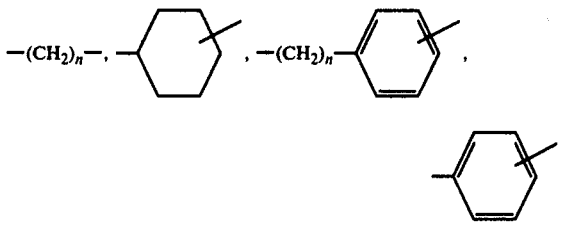

where n stands for a number from 1 to 4 and the aromatic radicals may contain further substituents, or the radicals

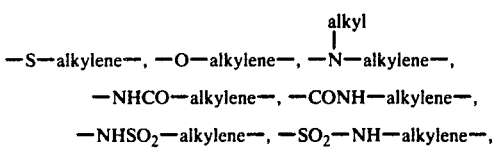

-continued

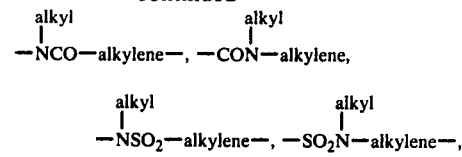

—CO—alkylene—, —COO—alkylene—, —alkylene—O—alkylene—, —alkylene—S—alkylene—, —alkylene—NHCO—alkylene—, alkylene—CONH—alkylene—, alkylene—SO$_2$NH—alkylene—, —alkylene—NHSO$_2$—alkylene, alkylene—OCO—alkylene, where "alkyl" stands for an alkyl group with 1–4 carbon atoms and "alkylene" stands for an alkylene group with 1–4 carbon atoms.

The new dyestuffs can be prepared by reacting compounds of the formula

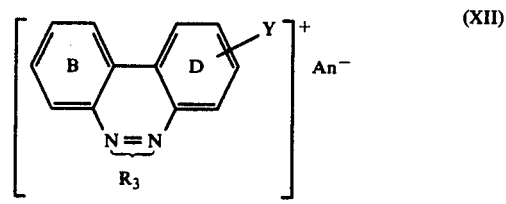

in which the rings B and D may contain further non-ionic substituents; $R_3$ stands for an alkyl, aralkyl, alkenyl, alkoxy or aralkoxy radical; An$^-$ represents an anionic radical; and Y stands for a radical which can be split off, optionally with the addition of dehydrating agents, with compounds of the formula

or HOR$_2'$ (XIV) or HSR$_2'$ (XV) or with the anions of the hydroxy or thio compounds, in which $R_1$ stands for hydrogen, alkyl, aralkyl, alkenyl, aryl, NH$_2$, or for a heterocyclic radical; $R_2$ means hydrogen, alkyl, aralkyl, aryl or a heterocyclic radical; the radicals $R_1$ and $R_2$ may also be cyclised with the formation of a hetero ring; $R_2'$ means an alkyl, aralkyl or aryl radical, and, if desired, subsequently quaternising the amino groups in external position.

The term "quaternisation" in the meaning of the invention refers to the conversion of a primary, secondary or tertiary amino group into a quaternary ammonium group, for example, by the reaction with alkylating agents, such as alkyl halides, dialkyl sulphates; or with chloramine (NH$_2$Cl) to form the corresponding hydrazinium compounds; or by the reaction with acrylonitrile (to form β-cyanoethyl-ammonium groups) or arylsulphonic acid esters or acrylamides.

Compounds of the formula (XII) suitable for the process are, for example, the compounds of the following Table:

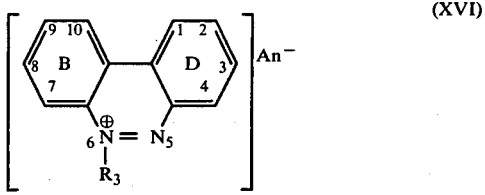

(XVI)

| R_3 | Substituent in ring B | Substituent in ring D |
|---|---|---|
| —CH_3 | — | 1-Cl |
| —C_2H_5 | — | 2-F |
| —CH_3 | — | 2-OCH_3 |
| —CH_3 | — | 1-Br |
| —CH_3 | — | 2-OC_2H_5 |
| —CH_3 | — | 1-CH_3—2-CH_3S— |
| —CH_3 | — | 3-Cl |
| —C_2H_5 | — | 2-Cl, 4-Cl |
| —CH_3 | — | 2-Br, 4-Br |
| —C_2H_4OH | 9-Cl, 8-CH_3 | 2-Cl |
| —CH_3 | 9-Cl | 2-Cl |
| —CH_3 | 7-CH_3 | 2-Cl, 4-Cl |
| —C_2H_4CN | 9-Cl | 2-Cl |
| —CH_3 | 9-CONH_2 | 2-Cl |
| —CH_3 | 7-COOCH_3 | 2-Cl |
| —CH_3 | 9-NO_2 | 2-Cl |
| —CH_2CH=CH_2 | 9-Cl | 2-Cl |
| —CH_3 | — | 2-OC_3H_7(n) |
| —CH_3 | 9-OCH_3 | 2-OCH_3, 1-NO_2 |
| —C_4H_9 | 9-Cl | 2-Cl |
| -benzyl | 9-OCH_3 | 2-OCH_3, 4-SO_2NH_2 |
| —CH_3 | 9-SO_2CH_3 | 2-SO_2CH_3 |
| —CH_3 | 9-benzyl . S— | 2-benzyl . S— |
| —CH_3 | — | 2-Br |
| —CH_3 | — | 2,3-dichloro |
| —CH_3 | 7-Br | 4-Br |
| —CH_3 | 9-CH_3 7-Br | 2-CH_3 4-Br |
| —CH_3 | 8-CH_3 9-Cl | 3-CH_3 2-Cl |
| —CH_3 | — | — |
| —C_2H_5 | — | — |
| -benzyl | — | — |
| —OCH_3 | 9-Cl | 2-Cl |
| —OCH_3 | 9-Br | 2-Br |
| —OCH_3 | — | 2-Br |
| —OC_2H_5 | — | 2-Br 4-Br |
| —OCH_3 | 9-Cl 8-CH_3 | 2-Cl 3-CH_3 |
| —O-benzyl | 9-Cl | 2-Cl |

The non-quaternised preliminary products of the formula (X) or (XII) can be obtained from suitable o,o'-di-substituted diphenyl derivatives. When o,o'-dinitro-diphenyl compounds are used, the nitro groups are converted into the benzo[c]cinnoline system; for example, by alkaline reduction with the use of catalytic hydrogen and a palladium-charcoal catalyst system.

Compounds of the benzo[c]cinnoline system can also be obtained by the catalytic reduction of o,o'-dinitro-diphenyl compounds to o,o'-diamino-diphenyl compounds, for example, with hydrazine hydrate and Raney nickel, and subsequent oxidative linkage, e.g. with sodium perborate in glacial acetic acid. Other ways are the reduction of o,o'-dinitro-diphenyl, for example, with sodium sulphide to form the benzo[c]cinnoline-6-oxide compounds, or the electrolytic reduction of o,o'-dinitro-diphenyls or their reduction with Na-amalga or zinc dust in an alkaline alcoholic-aqueous medium.

Some of the non-quaternised benzo[c]cinnoline compounds are known from H. Stetter, M. Schwarz, Berichte 90 (1975), 1351; F. E. King, T. J. King, J. Chem. Soc. 1945, 825; J. F. Corbett, P. F. Holt, J. Chem. Soc. 1961, 5035; J. F. Corbett, P. F. Holt, J. Chem. Soc. 1961, 3698; J. F. Corbett, P. F. Holt, A. N. Hughes, M. Vickery, J. Chem. Soc. 1962, 1823; G. E. Lewis, J. A. Reiss, Aust. J. Chem. 20 (1967), 2217. When these compounds are treated with quaternising agents, particularly with alkylating agents, there are obtained compounds (X) or (XII). The quaternisation, e.g. alkylation can be carried out by heating solutions or suspensions of the non-quaternised compounds in an inert medium with an alkylating agent at 60°–150° C., preferably at 80°–120° C. The alkylating agent may also be used in excess as solvent.

Suitable inert media are, for example, organic liquids, such as benzine, ligroin, cyclohexane, benzene, toluene, chloroform, chlorobenzene, dichlorobenzene, nitrobenzene, tetralin, dioxan, acetone, methyl ethyl ketone and dimethyl formamide.

Suitable alkylating agents are, for example, dimethyl sulphate, diethyl sulphate, di-n-butyl sulphate, di-iso-amyl sulphate, dimethyl pyrosulphate; benzene-sulphonic acid methyl, ethyl, n-propyl, iso-propyl and iso-butyl ester; p-toluene-sulphonic acid methyl, ethyl, n-propyl, iso-propyl and iso-butyl ester; chloromethane, bromomethane, iodomethane, chloroethane, bromoethane, iodoethane, 1-chloropropane, 1-bromopropane, 1-iodopropane, 2-chloropropane, 2-bromopropane, 2-iodopropane, 1-bromobutane, 1-chlorobutane, 1-iodobutane, 1-bromo-2-methylpropane, 1-chloro-2-methylpropane, 1-chloropentane, 1-bromopentane, 1-iodopentane, 1-chlorohexane, 1-bromohexane, 1-iodohexane, bromocyclohexane, 1-bromoheptane, 1-bromoctane, 1-iodoctane, 2-iodoctane, 1-bromodecane, 1-bromododecane; benzyl chloride, benzyl bromide, allyl chloride, allyl bromide, 2-bromo- and 2-chloro-diethyl ether; as well as chloro- and bromo-acetic acid esters, such as chloro- and bromo-acetic acid ethyl ester; ethyleneoxide, acrylamide and acrylonitrile.

The alkylation can also be carried out in the presence of alkaline agents, especially in the presence of tertiary amines carrying space-filling substituents on the nitrogen atom, according to Belgian Patent Specification No. 735,565. Tri-isopropanolamine is a particularly suitable amine with space-filling substituents.

Suitable exchangeable radicals Y in the compounds (XII) are primarily hydrogen; the sulphonic acid group; halogen atoms, such as fluorine, chloride and bromine; alkoxy groups, such as methoxy, ethoxy, p-methoxye-thoxy, n-propoxy, iso-propoxy, n-butoxy, iso-butoxy, n-pentoxy, 2-methyl-butoxy-1,3-methyl-butoxy-1, 2,2-dimethyl-propoxy-1, n-hexoxy and n-dodecyloxy; aralkoxy radicals, such as benzyloxy; aryloxy radicals, such as phenyloxy, 4-nitro-phenyloxy and 4-methylphenyloxy; alkylthio radicals, such as methylthio, ethylthio, n-propylthio, iso-propylthio, n-butylthio, iso-butylthio, n-pentylthio and n-hexylthio; alkylsulphonyl groups, such as methylsulphonyl, ethylsulphonyl, n-propylsulphonyl, iso-propylsulphonyl, n-butylsulphonyl, iso-butylsulphonyl, n-pentylsulphonyl and n-hexylsulphonyl; or arylsulphonyl groups, such as phenylsulphonyl, 4-methyl-phenylsulphonyl, 4-chloro-phenylsulphonyl, 2-methyl-phenylsulphonyl, 2-chloro-phenylsulphonyl, 2-ethyl-4-chloro-phenylsulphonyl and 4-acetylaminophenylsulphonyl.

Further suitable exchangeable radicals Y are alkylsulphonic acid radicals, such as methane-sulphonate, chloromethane-sulphonate, ethane-sulphonate, n-propane-sulphonate, iso-propane-sulphonate, n-butane-sulphonate, iso-butane-sulphonate, n-pentane-sulphonate and n-hexane-sulphonate; aralkyl-sulphonic acid radicals, such as benzyl-sulphonate, 4-methylbenzyl-sulphonate, 4-chlorobenzyl-sulphonate, 2-methylbenzyl-sulphonate, 2-chlorobenzyl-sulphonate, 2-methyl-4-chlorobenzylsulphonate, 4-nitrobenzyl-sulphonate, 2-phenylethylsulphonate and 2-4'-methyl-phenylethyl-sulphonate; and arylsulphonic acid radicals, such as phenyl-sulphonate, 4-methyl-phenyl-sulphonate, 4-chlorophenyl-sulphonate, 2-methylphenyl-sulphonate, 2-chlorophenyl-sulphonate and 2-methyl-4-chlorophenyl-sulphonate.

If in the reaction of compounds (XII) with compounds (XIV) or (XV) the latter are reacted in the form of their anions, then the alkali metal, magnesium or calcium salts of the alcohols or thio compounds are used, for example.

Compounds (XIII) suitable for condensation with compounds (XII) are, for example: aniline, N-methyl-aniline, N-ethyl-aniline, N-butyl-aniline, N-iso-butyl-aniline, 2-chloro-aniline, N-ethyl-2-chloro-aniline, 3-chloro-aniline, 4-chloro-aniline, 2,3-dichloro-aniline, 2,4-dichloro-aniline, 3,4-dichloro-aniline, 2,5-dichloro-aniline, 3,5-dichloro-aniline, 3,4,6-trichloro-aniline, 2-nitro-aniline, 3-nitro-aniline, N-methyl-3-nitro-aniline, 4-nitro-aniline, N-methyl-4-nitro-aniline, 4-chloro-2-nitro-aniline, 5-chloro-2-nitro-aniline, 4-chloro-3-nitro-aniline, 2-chloro-4-nitro-aniline, 2-bromo-4-nitro-aniline, 2,5-dichloro-4-nitro-aniline, 2-amino-toluene, 2-N-methylamino-toluene, 2-N-ethylamino-toluene, 2-N-benzylamino-toluene, 3-chloro-2-amino-toluene, 4-chloro-2-amino-toluene, 5-chloro-2-amino-toluene, 6-chloro-2-amino-toluene, 4,5-dichloro-2-amino-toluene, 4-nitro-2-amino-toluene, 4-nitro-2-(N-methylamino)-toluene, 4-nitro-2-(N-ethylamino)-toluene, 5-chloro-2-amino-benzotrifluoride, 5-nitro-2-amino-toluene, 6-nitro-2-amino-toluene, 3-amino-toluene, 3-N-ethylamino-toluene, 3-N-n-butylamino-toluene, 4-chloro-3-amino-toluene, 4-chloro-3-amino-benzotrifluoride, 6-chloro-3-amino-toluene, 4,6-dichloro-3-amino-toluene, 4-amino-toluene, 4-N-methylamino-toluene, 4-N-ethylamino-toluene, 2-chloro-4-amino-toluene, 2-nitro-4-amino-toluene, benzylamine, methylbenzylamine, N-benzylaniline, 2-N-benzylamino-toluene, 2-amino-1-ethylbenzene, 3-amino-1,2-dimethylbenzene, 4-amino-1,3-dimethylbenzene, 6-nitro-4-amino-1,3-dimethylbenzene, 5-amino-1,3-dimethylbenzene, 2-amino-1,4-dimethylbenzene, 2-amino-3-methyl-1-ethylbenzene, 4-amino-1,2-dimethylbenzene, '4-amino-5-ethyl-1,3-dimethylbenzene, 5-amino-1,2,4-trimethylbenzene, 4-amino-1,3,5-trimethylbenzene, 2-amino-1,3-diethylbenzene, 2-amino-5-methyl-1,3-diethylbenzene, 4-amino-3-methyl-1-cyclohexylbenzene, [1,2-diamino-benzene, 4-nitro-1,2-diaminobenzene, 1-amino-2-acetoanilide, 1,3-diaminobenzene,] N,N-dimethyl-phenylene-diamine-(1,3), [N-formyl-phenylene-diamine-(1,3), N-acetyl-phenylene-diamine-(1,3),] N,N-diethyl-N'-acetyl-phenylene-diamine-(1,3), [N-(3'-amino-benzoyl)-phenylene-diamine-(1,3), (3-amino-phenyl)-oxamic acid, 4-chloro-phenylene-diamine-(1,3), 4-nitro-phenylene-diamine-(1,3), 1,4-diamino-benzene, N-methyl-phenylene-diamine-(1,4), phenylene-diamine-(1,4), N,N-dimethyl-phenylene-diamine-(1,4), N,N-diethyl-phenylene-diamine-(1,4), N-formyl-phenylene-diamine-(1,4), (N-methyl-N-formyl)-phenylene-diamine-(1,4), N-acetyl-phenylene-diamine-(1,4), (N-methyl-N-acetyl)-phenylene-diamine-(1,4), (N-ethyl-N-acetyl)-phenylene-diamine-(1,4), (N-cyclohexyl-N-acetyl)-phenylene-diamine-(1,4), (4-aminophenyl)-oxamic acid, glycollic acid-(4-amino-anilide), 2-chloro-phenylene-diamine-(1,4), 2,5-dichloro-phenylene-diamine-(1,4), 2,6-dichloro-phenylene-diamine-(1,4), 2-nitro-phenylene-diamine-(1,4), 2-nitro-4-acetamino-1-amino-benzene, 2,4-diamino-1-methyl-benzene, 2-(N-ethylamino)-4-amino-2-methyl-benzene, 2-(N-acetylamino)-4-amino-1-methyl-benzene, 2,5-diamino-1-methyl-benzene, 5-(N-acetylamino)-2-amino-1-methyl-benzene, 2,6-diamino-1-methyl-benzene, 5-benzoylamino-2-amino-4-chloro-1-methyl-benzene, 4-aminobenzyl-dimethylamine,]2-amino-1-methoxy-benzene, 2-amino-1-phenoxy-benzene, 4-chloro-2-amino-anisole, 5-chloro-2-amino-anisole, 4,6-dichloro-2-amino-diphenyl ether, 4-nitro-2-amino-anisole, 3-amino-1-methoxy-benzene, 4-amino-anisole, 4-amino-phenetole, [4,4-diamino-diphenyl ether, 3-nitro-4-amino-anisole, 2,4-diamino-anisole, 2-acetamino-5-amino-anisole, 3-amino-4-acetamino-phenetole,]4-amino-2-methoxy-1-methyl-benzene, 2-amino-4-methoxy-1-methyl-benzene, 3-amino-4-methoxy-1-methyl-benzene, 3-amino-4-ethoxy-1-methyl-benzene, 2-amino-1,4-dimethoxy-benzene, 2-amino-1,4-diethoxy-benzene, 5-nitro-2-amino-1,4-dimethoxy-benzene, 3-amino-benzonitrile, 4-amino-benzoic acid amide, 4-amino-benzoic acid methyl ester, 4-amino-benzoic acid ethyl ester, 4-amino-benzoic acid-N-dodecyl ester, 4-amino-benzoic acid-N-butyl ester, 4-tert.-butyl-aniline, 4-amino-benzoic acid cyclohexyl ester, 3-amino-4-methyl-benzoic acid methyl ester, 3-amino-cimmamic acid, 3,4-dicyano-aniline, 5-amino-benzene-dicarboxylic acid-(1,3)-dimethyl ester, 1-amino-naphthalene, 1-ethylamino-naphthalene, [naphthalene-diamine-(1,5), naphthalene-diamine-(1,8)], 1-amino-naphthol-(3), 1-amino-naphthol-(5), 1-amino-naphthol-(7), 2-amino-diphenylamine, [4-chloro-2-amino-diphenylamine, 4-amino-diphenylamine, 4-amino-4'-methoxy-diphenylamine, 4,4'-diphenylamine, 4-amino-3-methoxy-diphenylamine, 4,4'-diamino-3,5'-dimethoxy-diphenyl, 2,2'-dichloro-4,4'-diamino-diphenyl, 4,4'-diamino-2,2'-dimethyl-diphenyl, 4,4'-diamino-diphenylmethane,] β-phenyl-ethylamine, N,N-diphenylamine, 1-amino-1-phenyl ether, methylamine, ethylamine, propylamine, isopropylamine, N-n-butylamine, cyclohexylamine, N-methylamine, N-octylamine, glucosamine, ethanolamine, diethanolamine, cyano-ethylamine, dodecylamine, N,N-dimethylamine, N,N-diethylamine, N-methyl-N-ethylamine, 2-ethyl-n-hexylamine, tert.-butylamine, stearylamine, N-methyl-stearylamine, allylamine, [ethylene-diamine, N,N-dimethyl-ethylene-diamine,] 1-amino-3-dimethylamino-propane, 1-amino-3-diethylamino-propane, N-methyl-ethanolamine, 1-amino-butanol-(3), 3-methoxy-propylamine-(1), 3-hydroxyl-propylamine, 2-amino-2-methyl-propane-diol-(1,3), morpholine, piperidine, piperazine, pyrrolidine, imidazoline, tetrahydroquinoline, 8-amino-quinoline, 6-amino-quinoxaline, 2-amino-benzimidazole, 2-methyl-dihydroindole, 2-methyl-indole, 2-amino-benzothiazole, 3-phenyl-pyrazoline-(Δ 2), 3-(4'-methylphenyl)-pyrazoline-(Δ 2), 3-(2'-ethylphenyl)-pyrazoline-(Δ 2), 3-(4'-isopropylphenyl)-pyrazoline-(Δ 2), 3-(4'-tert.-butylphenyl)-pyrazoline-(Δ 2), 3-(4'-cyclohexylphenyl)-pyrazoline-(Δ 2), 3-(4'-biphenylyl)-pyrazoline-(Δ 2), 3-(4'-chlorophenyl)-pyrazoline-(Δ 2), 3-(3'-chlorophenyl)-pyrazoline-(Δ 2), 3-(2'-chlorophenyl)-pyrazoline-(Δ 2), 3-(2',4'-dichlorophenyl)-pyrazoline-(Δ 2), 3-(3',4'-dichlorophenyl)-pyrazoline-(Δ 2), 3-(4'-bromophenyl)-pyrazoline-(Δ 2), 3-(4'-fluorophenyl)-pyrazoline-(Δ 2), 3-(4'-trifluoromethyl)-pyrazoline-(Δ 2), 3-(4'-acetylphenyl)-pyrazoline-(Δ 2), 3-(4'-cyanophenyl)-pyrazoline-(Δ 2), 3-(4'-methoxycarbonylphenyl)-pyrazoline-(Δ 2), 3-(4'-ethoxycarbonylphenyl)-pyrazoline-(Δ 2), 3-(4'-methylsulphonylphenyl)-pyrazoline-(Δ

2), 3-(4'-methylsulphonylaminophenyl)-pyrazoline-(Δ 2), 3-(4'-methoxyphenyl)-pyrazoline-(Δ 2), 3-(4'-ethoxyphenyl)-pyrazoline-(Δ 2), 3-(4'-phenoxyphenyl)-pyrazoline-(Δ 2), 3-(4'-isopropoxyphenyl)-pyrazoline-(Δ 2), 3-(styryl-5-phenyl)-pyrazoline-(Δ 2), 3-(p-chlorostyryl)-5-(4-chlorophenyl)-pyrazoline-(Δ 2), 3-(o,p-dichlorostyryl)-5-(2',4'-dichlorophenyl)-pyrazoline-(Δ 2), 3-(2'-thienyl)-pyrazoline-(Δ 2), 3-(5'-methylthienyl-2')-pyrazoline-(Δ 2), 3-(2'-furyl)-pyrazoline-(Δ 2), 3-[5'-(o,p-dichlorophenyl)-furyl-2']-pyrazoline-(Δ 2), 3-(4'-pyridyl)-pyrazoline-(Δ 2), 3-(2'-benzoxazolyl)-pyrazoline-(Δ 2), 3-(2'-benzothiazolyl)-pyrazoline-(Δ 2), 3-(1'-naphthyl)-pyrazoline-(Δ 2), 3-(2'-naphthyl)-pyrazoline-(Δ 2), 3-phenyl-4,5-tetramethylene-pyrazoline-(Δ 2), 3,4-diphenyl-pyrazoline-(Δ 2), 3,5-diphenyl-pyrazoline-(Δ 2) and the pyrazoline derivative of the formula

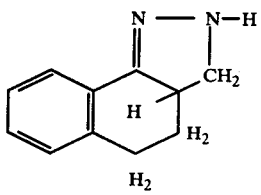

2,4,6-triamino-pyrimidine, 3-amino-1,3,4-triazole, 3-amino-1,2,4-triazole-5-carboxylic acid ethyl ester, 4-amino-azobenzene, 4-methoxy-4-amino-azobenzene, 4-nitro-4-amino-azobenzene, 4-amino-3-methoxy-6-methyl-azobenzene, mercapto-ethanol, hydrazine, mono-methyl-hydrazine, N,N-dimethyl-hydrazine, phenyl-hydrazine, p-methoxy-hydrazine, 2-nitrophenyl-hydrazine, 2,4-dinitrophenyl-hydrazine, semicarbazide, thiosemicarbazide, carbohydrazide, benzohydrazide, acetohydrazide.

Alcohols of the formula (XIV) suitable for condensation with compounds (XII) are, for example, methanol, ethanol, n-propanol, iso-propanol, n-butanol, iso-butanol, n-pentanol, n-hexanol, cyclohexanol and n-octanol; benzyl alcohol, 2-phenyl-ethanol, 4-methylbenzyl alcohol, 2-methylbenzyl alcohol, 4-nitrobenzyl alcohol and 4-chlorobenzyl alcohol; as well as phenols, such as phenol, 4-nitrophenol, 4-aminophenol, 4-methylphenol, 3-methylphenol, α-naphthol and β-naphthol.

Suitable compounds of the formula (XV) are, for example: methylmercaptan, ethylmercaptan, n-propylmercaptan, iso-propylmercaptan, n-butylmercaptan, iso-butylmercaptan, n-hexylmethylmercaptan, benzylmercaptan, 4-nitrophenylmercaptan, phenylmercaptan, 4-methylphenylmercaptan, 2-methylphenylmercaptan, 4-chlorophenylmercaptan and 4-nitrophenylmercaptan.

Suitable dehydrating agents are, for example, potassium and sodium hexacyanoferrate(III) and haloamides, such as N-bromosuccinimide, N-chloro-p-toluene-sulphonamide and N,N-dichloro-p-toluene-sulphonamide; iron(III) and copper(II) salts; alkali metal dicarbonates; lead(IV) oxide and its salts, e.g. lead tetra-acetate; and peroxy compounds such as hydrogen peroxide or sodium perborate.

Compounds of the formula (XII) can be reacted with compounds of the formulae (XIII), (XIV) or (XV) in an aqueous solution or suspension. The addition of an organic solvent may further the course of the reaction, especially when waterinsoluble or very weakly basic amines are used. Suitable organic solvents are, for example, acetone, methyl ethyl ketone, acetonitrile, dimethyl formamide, dimethyl sulphoxide, hexamethyl-phosphoric acid amide, nitromethane, 2-nitropropane, nitrobenzene, chlorobenzene, and di- and tri-chlorobenzenes. Occasionally it is advisable to carry out the reaction in an organic phase. However, the reaction can also be carried out without solvents; in this case, an excess of a compound of the formulae (XIII), (XIV) or (XV) is frequently desirable. The temperature limits of the reaction are predetermined by the solidification point of the mixture or of the components (XIII), (XIV) or (XV), on the one hand, and by the beginning (thermal) decomposition of the starting components or of the resultant products, on the other hand. It is recommended to carry out the reaction at temperatures of between 0° and 150° C., preferably at temperatures between 20° and 100° C. Temperatures between 20° and 80° C. are frequently optimal for the course of the reaction. If the compounds of the formulae (XIII), (XIV) or (XV) are used in the gaseous or vapour state, such as methylamine at 20° C., then the reaction can also be performed under pressure.

Another way of preparing the new dyestuffs consists in that compounds of the formulae

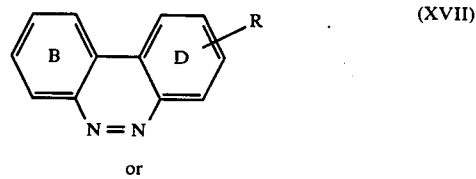

or

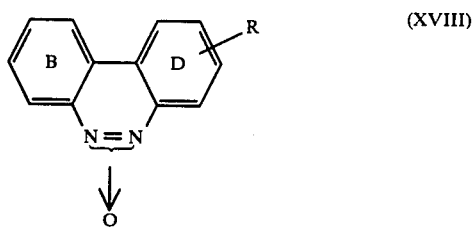

in which the rings B and D and the radical R have the same meaning as above (but in the case where, within the scope of the definition of R, the radical $R_2$ on page 1 stands for the formula (II), (II) is here present in the form of the non-quaternised compound without $R_3$ and $An^-$), are alkylated or quaternised.

Suitable compounds of the formula (XVII) are, for example: 1-anilino-, 2-anilino-, 3-anilino-, 4-anilino-, 8-anilino-, 9-anilino-, 2-anilino-3-methoxy-, 2-anilino-8-methoxy-, 2-anilino-9-methoxy-, 2-anilino-3-methyl-, 2-anilino-8-methyl-, 2-anilino-3-cyano-, 2-anilino-9-cyano-, 2-anilino-3-chloro-, 2-anilino-9-chloro-, 2-anilino-3,9-dichloro-, 2-anilino-3-bromo-, 2-anilino-8-bromo-, 2-anilino-9-bromo-, 2-anilino-3,8-dibromo-, 2-anilino-8,9-dibromo-, 2-N-methylanilino-, 2-N-methylanilino-3-chloro-, 2-N-methylanilino-8-chloro-, 2-N-methylanilino-9-chloro-, 2-N-methylanilino-3,9-dichloro-, 2-N-methylanilino-3-cyano-, 2-N-methylanilino-9-cyano-, 2-N-methylanilino-3,9-dibromo-, 2-N-methylanilino-8-nitro-, 1-methyl-2-N-ethylanilino-, 2-N-ethylanilino-8-methyl-, 2-N-ethylanilino-9-cyano-, 3-N-ethylanilino-, 2-N-butylanilino-8-nitro-, 2-N-butylanilino-3-methoxy-, 2-N-ethylanilino-9-methoxy-, 2-N-butylanilino-, 2-N-iso-butylanilino-, 2-N-iso-butylanilino-9-chloro-, 1-[2'-chloroanilino]-, 2-[2'-chloroanilino]-, 2-[2'-chloroanilino]-8-methyl-, 2-[2'-chloroanilino]-8-chloro-, 2-[4'-nitroanilino]-8-methyl-, 2-N-methyl-4'-nitroanilino-, 2-N-methyl-4'-nitroanilino-8-methyl-, 2-

[4'-chloro-2'-nitroanilino]-9-chloro-, 2-[2'-methylanilino]-, 2-[2'-methylanilino]-8-methoxy-, 2-[6'-chloro-2'-methylanilino]-, 2-[4'-methylanilino]-, 2-[4'-methylanilino]-8-methyl-, 2-[4'-methylanilino]-9-chloro-, 1-benzylamino-, 2-benzylamino-, 3-benzylamino-, 2-N-benzylanilino-, 2-[2',4'-dimethyl-5-nitroanilino]-, 2-[2',4',6'-trimethylanilino]-, 2-[2'-methoxyanilino]-, 3-[2'-methoxyanilino]-, 3-[2'-phenoxyanilino]-, 2-[2'-acetoaminoanilino]-, 2-[2',5'-diethoxyanilino]-, 3-[2',5'-diethoxyanilino]-, 1-[3'-cyanoanilino]-, 2-[3'-cyanoanilino]-, 2-[4'-methoxycarbonylanilino]-, 2-[3',4'-dicyanoanilino]-, 3-[3',4'-dicyanoanilino]-, 2-[1'-aminonaphthyl]-, 2-[2'-phenylethylamino]-, N-ethylanilino-, 2-[N,N-diphenylamino]-, 1-methylamino-, 2-methylamino-, 2-methylamino-3-methyl-, 2-methylamino-8-chloro-, 2-methylamino-3-chloro-8-cyano-, 2-methylamino-9-nitro-, 3-methylamino-, 9-methylamino-, 2-ethylamino-3-methyl-, 2-ethylamino-9-tert.-butyl-, 2-n-propylamino-, 2-n-propylamino-8-methoxycarbonyl-, 3-n-propylamino-, 2-iso-propylamino-, 2-iso-propylamino-9-methoxy-, 2-N-n-butylamino-, 2-N-n-butylamino-9-chloro-, 2-N-cyclohexylamino-, 1-N,N-dimethylamino-, 1-N,N-diethylamino-, 1-N,N-diethylamino-3-methoxy-, 1-N,N-diethylamino-8-methoxy-, 1-N,N-diethylamino-3-methyl-, 1-N,N-diethylamino-3-ethoxy-, 1-N,N-diethylamino-8-ethoxy-, 1-N,N-diethylamino-3-cyano-, 1-N,N-diethylamino-9-cyano-, 1-N,N-diethylamino-3-nitro-, 1-N,N-diethylamino-9-nitro-, 1-N,N-diethylamino-8-methoxycarbonyl-, 1-N,N-diethylamino-8-methylcarbonyl-, 1-N,N-diethylamino-9-methylcarbonyl-, 1-N,N-diethylamino-8-hydroxy-, 2-N,N-diethylamino-, 2-N,N-diethylamino-3-methyl-, 2-N,N-diethylamino-8-methyl-, 2-N,N-diethylamino-9-methyl-, 2-N,N-diethylamino-8-tert.-butyl-, 2-N,N-diethylamino-3-cyano-, 2-N,N-diethylamino-8-cyano-, 2-N,N-diethylamino-9-nitro-, 2-N,N-diethylamino-8-methoxycarbonyl-, 2-N,N-diethylamino-9-methoxycarbonyl-, 2-N,N-diethylamino-8-methylcarbonyl-, 2-N,N-diethylamino-9-methylcarbonyl-, 2-N,N-diethylamino-8-sulphamoyl-, 3-N,N-diethylamino-, 1-methyl-3-N,N-diethylamino-, 3-N,N-diethylamino-8-methyl-, 3-N,N-diethylamino-9-methyl-, 3-N,N-diethylamino-9-cyano-, 3-N,N-diethylamino-9-nitro-, 2-N-methyl-N-ethylamino-, 2-N-methyl-N-ethylamino-8-methyl-, 2-morpholino-, 2-piperidino-, 2-imidazolyl-, 2-[3'-phenyl-pyrazolinyl-(Δ2')]-, 2-[3'-(4''-methylphenyl)-pyrazolinyl-(Δ2')]-, 2-[3'-(2''-ethylphenyl)-pyrazolinyl-(Δ2')]-, 2-[3'-(4''-isopropylphenyl)-pyrazolinyl-(Δ2')]-, 2-[3'-(4''-tert.-butylphenyl)-pyrazolinyl-(Δ2')]-, 2-[3'-(4''-cyclohexylphenyl)-pyrazolinyl-(Δ2')]-, 2-[3'-(4''-biphenylyl)-pyrazolinyl-(Δ2')]-, 2-[3'-(4''-chlorophenyl)-pyrazolinyl-(Δ2')]-, 2-[3'-(3''-chlorophenyl)-pyrazolinyl-(Δ2')]-, 2-[3'-(2''-chlorophenyl)-pyrazolinyl-(Δ2')]-, 2-[3'-(2'',4''-dichlorophenyl)-pyrazolinyl-(Δ2')]-, 2-[3'-(3'',4''-dichlorophenyl)-pyrazolinyl-(Δ2')]-, 2-[3'-(4''-bromophenyl)-pyrazolinyl-(Δ2')]-, 2-[3'-(3'',4''-dichlorophenyl)-pyrazolinyl-(Δ2')]-, 2-[3'-(4''-bromophenyl)-pyrazolinyl-(Δ2')]-, 2-[3'-(4''-fluorophenyl)-pyrazolinyl-(Δ2')]-, 2-[3'-(4''-difluoromethyl)-pyrazolinyl-(Δ2')]-, 2-[3'-(4''-acetylphenyl)-pyrazolinyl-(Δ2')]-, 2-[3'-(4''-cyanophenyl)-pyrazolinyl-(Δ2')]-, 2-[3'-(4''-methoxycarbonylphenyl)-pyrazolinyl-(Δ2')]-, 2-[3'-(4''-methoxyphenyl)-pyrazolinyl-(Δ2')]-, 2-[3'-(4''-ethoxyphenyl)-pyrazolinyl-(Δ2')]-, 2-[3'-(4''-phenoxyphenyl)-pyrazolinyl-(Δ2')]-, 2-[3'-(4''-isopropoxyphenyl)-pyrazolinyl-(Δ2')]-, 2-[3'-styryl-5'-phenyl-pyrazolinyl-(Δ2')]-, 2-[3'-(4''-chlorostyryl)-5'-(4''-chlorophenyl)-pyrazolinyl-(Δ2')]-, 2-[3'-(2'',4''-dichlorophenyl)-pyrazolinyl-(Δ2')]-, 2-[3'-2',4''-dichlorostyryl)-5'-(2'',4''-dichlorophenyl)-pyrazolinyl-(Δ2')]-, 2-[3'-(2''-thienyl)-pyrazolinyl-(Δ2')]-, 2-[3'-(5''-methylthionyl-2'')-pyrazolinyl-(Δ2')]-, 2-[3'-(2''-furyl)-pyrazolinyl-(Δ2')]-, 2-[3'-[5''-(o,p-dichlorophenyl)-furyl-2'']-pyrazolinyl-(Δ2')]-, 2-[3'-(4''-pyridyl)-pyrazolinyl-(Δ2')]-, 2-[3'-(2''-benzoxazolyl)-pyrazolinyl-(Δ2')]-, 2-[3'-(2''-benzothiazolyl)-pyrazolinyl-(Δ2')]-, 2-[3'-(1''-naphthyl)-pyrazolinyl-(Δ2')]-, 2-[3'-(2''-naphthyl)-pyrazolinyl-(Δ2')]-, 2-[3'-phenyl-4',5'-tetramethylene-pyrazolinyl-(Δ2')]-, 2-[3',4'-diphenyl-pyrazolinyl-(Δ2')]-, and 2-[3',5'-diphenyl-pyrazolinyl-(Δ2')]-benzo[c]cinnoline and the corresponding benzo[c]cinnoline-6-oxides.

Within the scope of the new dyestuffs, those products in which R stands for a group

or generally for a group

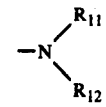

in which $R_{11}$ stands for hydrogen, an alkyl, aralkyl, alkenyl or aryl radical or a group $NH_2$; $R_{12}$ stands for hydrogen, an alkyl, aralkyl or aryl radical or for a group

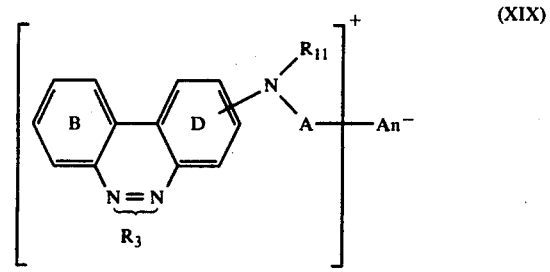

(XIX)

in which A, B, D, $R_3$ and $An^-$ have the same meaning as above, can also be prepared by converting in compounds of the general formula

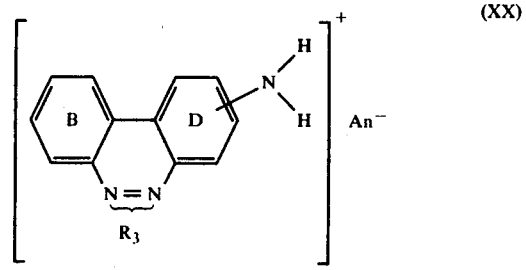

(XX)

in which the rings B and D, the radical $R_3$ and $An^-$ have the same meaning as above, the group

into a group

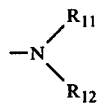

in a suitable manner, for example by alkylation, aralkylation, arylation, or by the introduction of a group $NH_2$ (which $ClNH_2$) and subsequent alkylation or quaternisation, if desired. In the above formulae (XIX) and (XX) the radicals $R_3$ preferably occupy the position indicated in the formula (III).

Suitable alkylating agents or aralkylating agents are the compounds already mentioned above.

Suitable arylating agents are primarily 2,4-dinitrochlorobenzene, 2,4-dinitro-fluorobenzene and 2,4-dinitro-bromobenzene.

The new dyestuffs of the formulae (I) to (IX) are valuable products which can be used for the dyeing and printing of textile and non-textile materials, for example, those of leather, tanned cotton, cellulose, synthetic superpolyamides and superpolyurethanes, as well as for the dyeing of lignincontaining fibres such as coconut, jute and sisal. They are further suitable for the production of writing liquids, stamping inks, pastes for ball point pens, and they can also be used in offset printing.

Materials suitable for dyeing with the basic dyestuffs of the general formulae (I) to (IX) are primarily loose material, fibres, filaments, ribbons, fabrics or knitted fabrics consisting of polyacrylonitrile or of copolymers of acrylonitrile (with an acrylonitrile proportion of at least 85%) with other vinyl compounds, such as vinyl chloride, vinylidene chloride, vinyl fluoride, vinyl acetate, vinyl-pyridine, vinyl-imidazole, vinyl alcohol, acrylic and methacrylic acid esters and amides, as. dicyanoethylene. Loose material, fibres, filaments, ribbons, fabrics or knitted fabrics of acid-modified synthetic materials, especially acid-modified aromatic polyesters and acid-modified polyamide fibres can also be dyed in an excellent way. Acid-modified aromatic polyesters are, for example, polycondensation products of sulphoterephthalic acid and ethylene glycol, i.e. polyethylene glycol terephthalates containing sulphonic acid groups (type DACRON 64 of E. I. DuPont de Nemours and Company), such as are described in Belgian Patent Specification No. 549,179 and U.S. Pat. Specification No. 2,893,816.

Dyeing can be carried out from a weakly acidic bath; it is expedient to introduce the material into the dyebath at 40° to 60° C. and then to dye at boiling temperature. It is also possible to dye under pressure at temperatures above 100° C. Furthermore, the dyestuffs can be added to spinning solutions for the production of fibres containing polyacrylonitrile, or they can be applied to the unstretched fibre.

The dyeings obtained with the dyestuffs of the formulae (I) and (III) to (IX) according to the invention on materials of polyacrylonitrile or acid-modified polyester fibres are characterised by very good fastness to light, wet processing, rubbing and sublimation and by a high affinity to the fibre. With anionic precipitating agents, such as alumina, tannin, phosphotungstic (molybdic) acids, the dyestuffs form pigments which are fast to light and can be used with advantage in paper printing.

The dyestuffs can be used individually or in mixtures. They are well suited for the dyeing of shaped articles consisting of polymers or copolymers of acrylonitrile, as. dicyanoethylene, acid-modified aromatic polyesters or acid-modified synthetic superpolyamides with the use of chlorinated hydrocarbons as dyebath, if they carry substituents which further the solubility in chlorinated hydrocarbons, such as e.g. the tert.-butyl group, or if the anion $An^-$ in the formulae (I) and (III) to (IX) is the anion of a monobasic organic acid with 4–30 carbon atoms.

Organic acids of this type are, for example, 2-ethylcaproic acid, lauric acid, oleic acid, linoleic acid; a mixture of aliphatic carboxylic acids with 15–19 carbon atoms (versatic acid 1519); a mixture of aliphatic carboxylic acids with 9–11 carbon atoms (versatic acid 911); coconut fatty acid first runnings, tetradecanic acid, undecylenic acid, dimethylpropanic acid, dimethylacetic acid; carboxylic acids the carbon chain of which is interrupted by hetero atoms, such as nonylphenol tetraethylene glycol ether-propionic acid, nonylphenol diethylene glycol ether-propionic acid, dodecyl tetraethylene glycol ether-propionic acid, 3-(nonyloxy)-propionic acid, 3-(isotridecyloxy)-propionic acid, 3-(isotridecyloxy)-diethylene glycol ether-propionic acid, ether-propionic acid of the alcohol mixture with 6–10 carbon atoms, nonylphenoxyacetic acid; aromatic carboxylic acids such as tert.-butylbenzoic acid; cycloaliphatic carboxylic acids such as hexahydrobenzoic acid, cyclohexene-carboxylic acid, abietic acid; and sulphonic acids such as tetrapropylene-benzenesulphonic acid.

Dyestuffs of the formulae (I) and (III) to (IX) in which the anion $An^-$ is the anion of one of the acids mentioned above, are particularly preferred.

If the dyestuffs according to the invention are present in the form of salts of the aforesaid monobasic organic acids with 4–30 carbon atoms, then it is possible to prepare quite stable solutions of these dyestuffs in chlorinated hydrocarbons, possibly with the addition of polar organic solvents which are completely miscible with chlorinated hydrocarbons, such as butyrolactone, dimethyl formamide, methanol, dioxan, acetonitrile, methyl ethyl ketone, nitrobenzene, dimethyl sulphoxide, benzonitrile, 2-nitrochlorobenzene.

To prepare solutions of this kind, the dyestuffs according to the invention, in the form of the free bases or as salts of organic acids with 4–30 carbon atoms, are stirred with chlorinated hydrocarbons and monobasic organic acids with 4–30 carbon atoms, possibly with the addition of polar organic solvents which are completely miscible with chlorinated hydrocarbons and optionally at an elevated temperature.

EXAMPLE 1

2 g aniline in 30 ml alcohol are added dropwise to a solution of 3.75 g 2,9-dichloro-N-methyl-benzo-[c]-cinnolinium methosulphate in 80 ml of water. A red dyestuff is formed. The mixture is stirred at room temperature for 2 hours and subsequently heated under reflux for 1 hour. When the mixture is cooling down, dark red crystals are precipitated; after drying, they are a red powder and dissolve in water with a red colour. The dyestuff cation of the probable formula

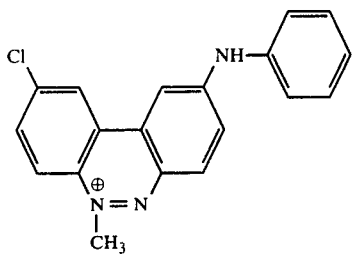

has methosulphate and chloride as anions.

The dyestuff dyes materials of polyacrylonitrile in red shades. The dyeings have excellent fastness to light and decatising.

When concentrated aqueous solutions of this dyestuff are mixed with excess amounts of a zinc chloride, Na-chloride, Na-bromide solution, a solution of Na-tetrafluoroborate, Na-perchlorate, Na-sulphate, Na-phosphate, Na-oxalate, then salts of the same dyestuff with the stated compensating ions are formed; they give the same shades on polyacrylonitrile.

If the cationic starting product in the above Example is replaced with a compound of the probable formula

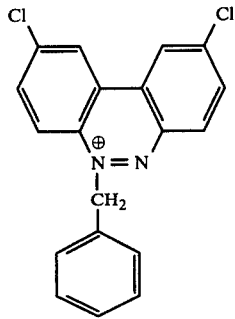

and the condensation is carried out with aniline as described, then a red dyestuff is again obtained, which dyes material of polyacrylonitrile in red shades.

EXAMPLE 2

2 g 4-amino-1-ethoxy-benzene in 30 ml alcohol are added dropwise to a solution of 3.75 g 2,9-dichloro-N-methylbenzo-[c]-cinnolinium methosulphate in 80 ml of water. A Bordeaux dyestuff is formed. The mixture is stirred at room temperature for 2 hours and subsequently heated under reflux for 1 hour.

When the mixture is cooling down, dark crystals are precipitated; after drying, they are a red powder and dissolve in water with a Bordeaux colour.

The dyestuff cation of the probable formula

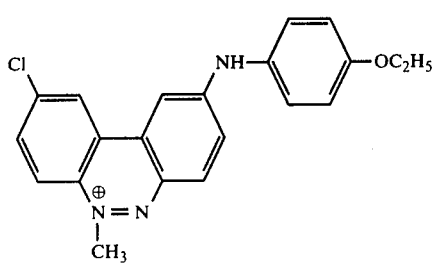

has methosulphate and chloride as anions.

The dyestuff dyes materials of polyacrylonitrile in Bordeaux shades. This dyestuff also can be converted into the other anions described in Example 1.

When the aniline in Example 1 is replaced with equivalent amounts of the amines listed in Column 1 of the following Table, then cationic dyestuff are likewise obtained which have the shades specified in Column 2.

| Column 1<br>Amine | Column 2<br>Shade on<br>Polyacrylonitrile |
|---|---|
| methylamine | orange |
| dimethylamine | " |
| diethylamine | " |
| cyanoethylamine | " |
| ethanolamine | " |
| diethanolamine | red-orange |
| iso-propylamine | " |
| n-butylamine | yellowish red |
| ethylene-diamine | orange |
| 3-amino-1-dimethylamino-propane | red-orange |
| aniline | red |
| 4-ethoxy-aniline | Bordeaux |
| 4-dimethylamino-aniline | brown-violet |
| 2-chloro-aniline | brown-red |
| 3-chloro-aniline | red |
| 4-chloro-aniline | yellowish red |
| 3-nitro-aniline | red-brown |
| 4-nitro-aniline | " |
| 2,4-dinitro-aniline | |
| o-toluidine | yellowish red |
| n-dodecylamine | orange |
| m-toluidine | bluish red |
| p-toluidine | red |
| o-phenylene-diamine | red-brown |
| m-phenylene-diamine | red |
| p-phenylene-diamine | violet |
| benzidine | |
| N-acetyl-p-phenylene-diamine | red |
| 2-amino-4-acetylamino-anisole | " |
| α-naphthylamine | brown-red |
| 1,5-diamino-naphthalene | red-brown |
| 4-amino-phenol | bluish red |
| anthranilic acid methyl ester | red-brown |
| 4-amino-benzoic acid methyl ester | red |
| 4-amino-azobenzene | red-brown |
| 4-amino-diphenylamine | black |
| 2,4-dimethoxy-aniline | red |
| N-methyl-aniline | " |
| N-ethyl-n-toluidine | orange-red |
| 4,4'-diamino-diphenyl ether | bluish red |
| 4-amino-4'-methoxy-diphenylamine | black |
| benzylamine | brown-red |
| 2-methyl-dihydro-(2,3)-indole | violet |
| 2-amino-benzothiazole | orange-red |
| 3-amino-1,2,4-triazole | red-orange |
| imidazole | orange |
| 1,2,3,4-tetrahydroquinoline | brown |
| 2-amino-pyridine | orange |
| 3-amino-pyridine | " |
| 4-amino-pyridine-N-oxide | yellow |
| piperidine | yellow-orange |
| pyrrolidine | red-orange |
| 3-phenyl-pyrazoline-(Δ2) | red |
| 3-4'-methylphenyl-pyrazoline-(Δ2) | " |
| 3-4'-ethylphenyl-pyrazoline-(Δ2) | " |
| 3-3'-methylphenyl-pyrazoline-(Δ2) | " |
| 3-4'-methylsulphonyl-pyrazoline-(Δ2) | " |
| 3-4'-methoxyphenyl-pyrazoline-(Δ2) | " |
| 3-4'-ethoxyphenyl-pyrazoline-(Δ2) | " |
| 3-4'-n-butoxyphenyl-pyrazoline-(Δ2) | " |
| 3-4'-iso-amyloxyphenyl-pyrazoline-(Δ2) | " |
| 3-4'-trifluorophenyl-pyrazoline-(Δ2) | " |
| 3-4'-fluorophenyl-pyrazoline-(Δ2) | " |
| 3-4'-chlorophenyl-pyrazoline-(Δ2) | " |
| 3-4'-bromophenyl-pyrazoline-(Δ2) | " |
| 3-4'-cyanophenyl-pyrazoline-(Δ2) | " |
| 3-4'-(β-diethylaminoethoxy)-phenyl-pyrazoline-(Δ2) | " |
| 3-4'-α-thienyl-pyrazoline-(Δ2) | " |
| 3-4'-biphenylyl-pyrazoline-(Δ2) | " |
| 3-3',5'-dimethylphenyl-pyrazoline-(Δ2) | " |
| 3-3',4'-dimethoxyphenyl-pyrazoline-(Δ2) | " |
| 3-styryl-5-phenyl-pyrazoline-(Δ2) | " |

| Column 1<br>Amine | Column 2<br>Shade on<br>Polyacrylonitrile |
| --- | --- |
| 3-4'-chlorostyryl-4-4'-chlorophenyl-pyrazoline-(Δ2) | " |
| 3,4-diphenyl-pyrazoline-(Δ2) | " |
| 3,5-diphenyl-pyrazoline-(Δ2) | " |
| 3-phenyl-5,5-dimethyl-pyrazoline-(Δ2) | " |
| 3-phenyl-4,4-dimethyl-pyrazoline-(Δ2) | " |
| morpholine | orange |
| piperazine | " |
| cyclohexylamine | red-orange |
| N-methyl-cyclohexylamine | " |
| hydrazine | orange |
| N,N-dimethylhydrazine | " |
| phenylhydrazine | red |
| semicarbazide | yellowish red |
| o-anisidine | red |
| m-anisidine | " |
| p-anisidine | bluish red |

EXAMPLE 3

5 ml of a 50% aqueous dimethylamine solution are added to a solution of 3.75 g N-methyl-benzo-[c]-cinnolinium methosulphate in 80 ml of water. A solution of 4 g potassium hexacyanoferrate(III) in 20 ml of water is added dropwise and the mixture is heated under reflux for 2 hours. An orange dyestuff is formed, the cation of which has the probable formula

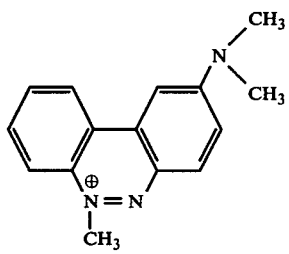

and which is precipitated by the addition of an aqueous 50% Zn-chloride solution in the form of the zinc chloride double salt.

The dyestuff dyes materials of polyacrylonitrile in orange shades. This dyestuff also can be converted into the other anions described in Example 1.

EXAMPLE 4

2 g aniline in 30 ml alcohol are added dropwise to a solution of 4 g 2-bromo-N-methoxy-benzo-[c]-cinnolinium methosulphate in 80 ml of water. A red dyestuff is formed. The mixture is stirred at room temperature for 2 hours and subsequently heated under reflux for 1 hour.

When the mixture cools down, dark crystals are precipitated, which dissolve in water with a red colour.

The dyestuff cation of the probable formula

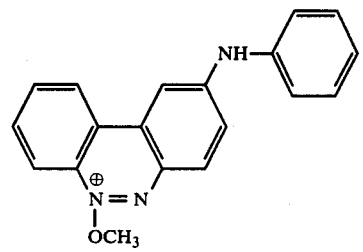

has methosulphate and bromide as anions.

The dyestuff dyes materials of polyacrylonitrile in yellowish red shades.

It can be converted into the other anions described in Example 1.

When the aniline is replaced in Example 4 with equivalent amounts of the amines listed in Column 1 of the following Table, then cationic dyestuffs are likewise obtained, which have the shades specified in Column 2.

| Amine | Shade on Polyacrylonitrile |
| --- | --- |
| aniline | yellowish red |
| o-toluidine | orange |
| m-toluidine | red-orange |
| 4-chloro-aniline | orange |
| p-phenylene-diamine | violet |
| N-acetyl-p-phenylene-diamine | red |
| 4,4'-diamino-diphenyl ether | orange |
| 4-amino-diphenylamine | violet |
| 4-amino-4'-methoxy-diphenylamine | violet |
| anthranilic acid methyl ester | red-orange |
| 2-methyl-dihydro-2,3-indole | violet |
| pyrrolidine | orange |
| morpholine | " |
| phenylhydrazine | " |
| benzidine | violet |
| o-anisidine | yellowish red |
| m-anisidine | " |
| p-anisidine | red |
| 3-phenyl-pyrazoline-(Δ2) | yellowish red |
| 3-4'-methylphenyl-pyrazoline-(Δ2) | " |
| 3-4'-ethylphenyl-pyrazoline-(Δ2) | " |
| 3-3'-methylphenyl-pyrazoline-(Δ2) | " |
| 3-4'-methylsulphonyl-pyrazoline-(Δ2) | " |
| 3-4'-methoxyphenyl-pyrazoline-(Δ2) | " |
| 3-4'-ethoxyphenyl-pyrazoline-(Δ2) | " |
| 3-4'-n-butoxyphenyl-pyrazoline-(Δ2) | " |
| 3-4'-iso-amyloxyphenyl-pyrazoline-(Δ2) | " |
| 3-4'trifluorophenyl-pyrazoline-(Δ2) | " |
| 3-4'-fluorophenyl-pyrazoline-(Δ2) | " |
| 3-4'-chlorophenyl-pyrazoline-(Δ2) | " |
| 3-4'-bromophenyl-pyrazoline-(Δ2) | " |
| 3-4'-cyanophenyl-pyrazoline-(Δ2) | " |
| 3-4'-(β-diethylaminoethoxy)-phenyl-pyrazoline-(Δ2) | " |
| 3-4'-α-thienyl-pyrazoline-(Δ2) | " |
| 3-4'-biphenylyl-pyrazoline-(Δ2) | " |
| 3-3',5'-dimethylphenyl-pyrazoline-(Δ2) | " |
| 3-3',4'-dimethoxyphenyl-pyrazoline-(Δ2) | yellowish red |
| 3-styryl-5-phenyl-pyrazoline-(Δ2) | " |
| 3-4'-chlorostyryl-4,4'-chlorophenyl-pyrazoline-(Δ2) | " |
| 3,4-diphenyl-pyrazoline-(Δ2) | " |
| 3,4-diphenyl-pyrazoline-(Δ2) | " |
| 3-phenyl-5,5-dimethyl-pyrazoline-(Δ2) | " |
| 3-phenyl-4,4-dimethyl-pyrazoline-(Δ2) | " |

EXAMPLE 5

2 g 2-mercapto-ethanol in 30 ml alcohol are added dropwise to a solution of 3.75 g 2,9-dichloro-N-methyl-benzo-[c]-cinnolinium methosulphate in 80 ml of water.

The mixture is stirred at room temperature for 2 hours and subsequently heated under reflux for 1 hour. When the mixture cools down, dark crystals are precipitated which dissolve in water in a reddish yellow colour.

The dyestuff cation of the probable formula

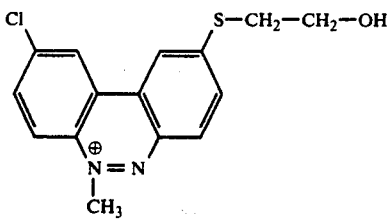

has methosulphate and chloride as anions.

The dyestuff dyes materials of polyacrylonitrile in reddish yellow shades.

This dyestuff can be converted into the other anions described in Example 1.

EXAMPLE 6

3 g 2-anilino-9-chloro-benzo-[c]-cinnoline are dissolved in 100 ml chlorobenzene, and 5 ml dimethyl sulphate are added. The mixture is boiled under reflux for 5 hours. When the mixture cools down, dark red crystals are precipitated which dissolve in water with a red colour.

The dyestuff has the probable formula

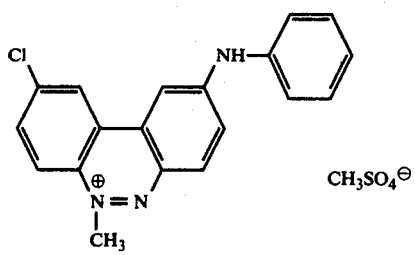

It dyes materials of polyacrylonitrile in red shades.

It can be converted into the other anions described in Example 1.

EXAMPLE 7

10 ml of a 1N sodium hydroxide solution and 10 ml dimethyl sulphate are added to a solution of 4.3 g 2-anilino-6-methyl-9-chloro-benzo-[c]-cinnolinium methosulphate in 100 ml of water. The mixture is stirred at 30° C. for 5 hours and subsequently heated under reflux for 1 hour. When the mixture has cooled down, the dyestuff of the following probable formula

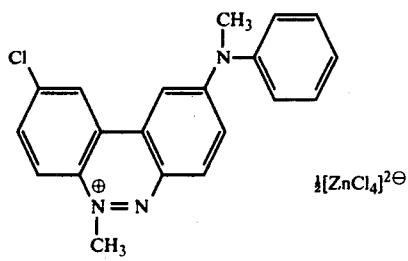

can be precipitated with a 50% zinc chloride solution in the form of the zinc chloride double salt. The dyestuff is a dark red powder. It dyes materials of polyacrylonitrile in yellowish red shades.

When the cationic starting compound is replaced in Example 1 with equivalent amounts of 2,9-dichloro-N-ethyl-benzo-[c]-cinnolinium ethylsulphate and the condensation is carried out with aniline as described, then a red dyestuff is again obtained which dyes material of polyacrylonitrile in red shades.

When the cationic starting compound is replaced in Example 4 with 2-chloro-N-methoxy-benzo-[c]-cinnolinium methosulphate, then the same dyestuff cation is obtained.

When the cationic starting compound is replaced in the above Example with equivalent amounts of 2-bromo-N-ethoxy-benzo-[c]-cinnolinium ethylsulphate or 2-bromo-N-benzyloxy-benzo-[c]-cinnolinium chloride and the condensation is carried out with aniline as described, then a dyestuff is again obtained which dyes material of polyacrylonitrile in yellowish red shades.

When the cationic starting compound is replaced in Example 5 with equivalent amounts of 2,9-dichloro-N-ethyl-benzo-[c]-cinnolinium ethylsulphate or 2,9-dichloro-N-benzyl-benzo-[c]-cinnolinium chloride and the condensation is carried out with 2-mercapto-ethanol as described, then a dyestuff is again obtained, which dyes material of polyacrylonitrile in reddish yellow shades.

EXAMPLE 8

5 g 2,9-dichloro-benzo-[c]-cinnoline are dissolved in 700 ml methyl ethyl ketone, 20 ml dimethyl sulphate are added dropwise, and the mixture is heated under reflux for 8 hours. When the mixture cools down, a yellow-brown water-soluble substance crystallises, which has the following probable formula

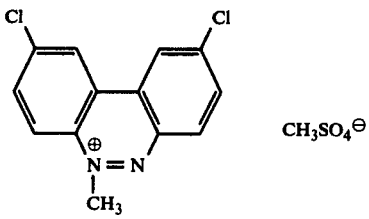

When the dimethyl sulphate is replaced in the above Example with equivalent amounts of diethyl sulphate or benzyl chloride and the quaternisation is carried out in chlorobenzene at 100°–120° C., then there is obtained the likewise water-soluble 2,9-dichloro-N-ethyl-benzo-[c]-cinnolinium ethylsulphate or 2,9-dichloro-N-benzyl-benzo-[c]-cinnolinium chloride.

To prepare the 2,9-dichloro-benzo-[c]-cinnoline, 2,2'-dinitro-5,5'-dichloro-biphenyl (lit: R. A. Abramovitch, B. A. Davis, J. Chem. Soc. C 1968, 125) is used as starting compound and the reduction is carried out (a) catalytically to form 2,2'-diamino-5,5'-dichloro-biphenyl which is then oxidised in analogy with the method of J. F. Corbett, P. F. Holt (J. Chem. Soc. 1961, 3698) with sodium perborate in glacial acetic acid to form 2,9-dichloro-benzo-[c]-cinnoline;

(b) catalytically in the alkaline range in analogy with the method of H. Stetter, M. Schwarz, Ber. 90, 1351 (1957) to form 2,9-dichloro-benzo-[c]-cinnoline;

(c) with iron oxalate according to the method of R. A. Abramovitch, B. A. Davis, J. Chem. Soc. C 1968, 125–126.

Furthermore, 2,9-dichloro-benzo-[c]-cinnoline is prepared according to the process described by J. F. Corbett, P. F. Holt, A. N. Hughes, M. Vickery (J. Chem. Soc. 1962, 1823) by the reduction of 2,9-dichloro-benzo-[c]-cinnoline-N-oxide with lithium aluminium hydride.

The 2,2'-diamino-5,5'-dichloro-biphenyl required for the oxidation method with sodium perborate described above is also prepared according to the method of D. Delfs [German Pat. No. 627,138 (1933), IG Farb; Frdl. 22, 895] where the azo dyestuff 2,4-dichloro-aniline→• naphthol-2-disulphonic acid-5,7 is dimerised and subsequently split on the azo group.

EXAMPLE 9

5 g 2,9-dibromo-benzo-[c]-cinnoline are dissolved in 700 ml methyl ethyl ketone, 20 ml dimethyl sulphate are added dropwise, and the mixture is heated under reflux for 8 hours. When the mixture cools down, a yellow-brown water-soluble substance crystallises, which has the following probable formula

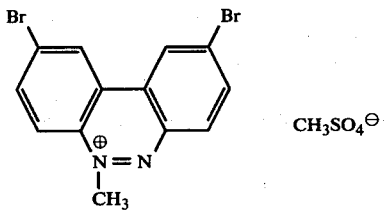

When the dimethyl sulphate is replaced in the above Example with equivalent amounts of diethyl sulphate or benzyl chloride and the quaternisation is carried out in chlorobenzene at 100°-120° C., then there is obtained the likewise water-soluble 2,9-dibromo-N-ethyl-benzo-[c]-cinnolinium ethylsulphate or 2,9-dibromo-N-benzo-[c]-cinnolinium chloride.

The 2,9-dibromo-benzo-[c]-cinnoline is prepared from the 2,2'-diamino-5,5'-dibromo-biphenyl described by Le Fevre (J. Chem. Soc. 1929, 736) according to the oxidation method with sodium perborate of J. F. Corbett, P. F. Holt (J. Chem. Soc. 1961, 3698).

EXAMPLE 10

5 g 2-bromo-benzo-[c]-cinnoline are dissolved in 600 ml methyl ethyl ketone, 20 ml dimethyl sulphate are added dropwise, and the mixture is heated under reflux for 8 hours. When the mixture cools down, a yellow-brown water-soluble substance crystallises, which has the following probable formula

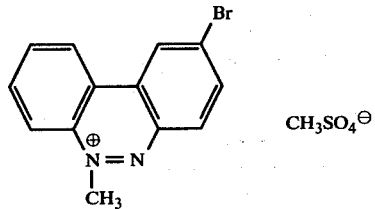

When the dimethyl sulphate is replaced in the above Example with equivalent amounts of diethyl sulphate or benzyl chloride and the quaternisation is carried out in chlorobenzene at 100°-120° C., then there is obtained the likewise water-soluble 2-bromo-N-ethyl-benzo-[c]-cinnolinium ethylsulphate or 2-bromo-N-benzyl-benzo-[c]-cinnolinium chloride.

The 2-bromo-benzo-[c]-cinnoline is prepared according to the process of J. F. Corbett, P. F. Holt (J. Chem. Soc. 1961, 5036).

EXAMPLE 11

5 g 2-chloro-benzo-[c]-cinnoline are dissolved in 600 ml of methyl ethyl ketone, 20 ml dimethyl sulphate are added dropwise, and the mixture is heated under reflux for 8 hours. When the mixture cools down, a yellow-brown water-soluble substance crystallises, which has the following probable formula

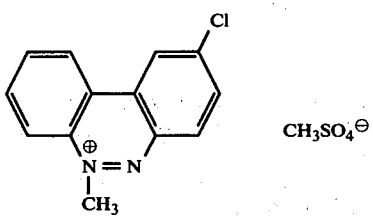

When the dimethyl sulphate is replaced in the above Example with equivalent amounts of diethyl sulphate or benzyl chloride and the quaternisation is carried out in chlorobenzene at 100°-120° C., then there is obtained the likewise water-soluble 2-chloro-N-ethyl-benzo-[c]-cinnolinium ethylsulphate or 2-chloro-N-benzyl-benzo-[c]-cinnolinium chloride.

The 2-chloro-benzo-[c]-cinnoline is prepared according to the process of G. M. Badger, J. R. Drewer, G. E. Lewis [Aust. J. Chem. 17, 1036 (1964)].

EXAMPLE 12

5 g 2,9-dichloro-3,8-dimethyl-benzo-[c]-cinnoline are dissolved in 500 ml chlorobenzene, 20 ml dimethyl sulphate are added dropwise, and the mixture is heated at 100°-120° C. for 8 hours. When the mixture cools down, a brown water-soluble substance crystallises, which has the following probable formula

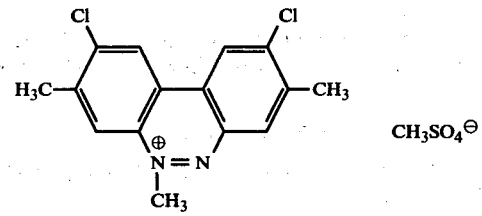

When the dimethyl sulphate is replaced in the above Example with equivalent amounts of diethyl sulphate or benzyl chloride and the quaternisation is carried out in chlorobenzene at 100°-120° C., then there is obtained the likewise water-soluble 2,9-dichloro-3,8-dimethyl-N-ethyl-benzo-[c]-cinnolinium ethylsulphate or 2,9-dichloro-3,8-dimethyl-N-benzyl-benzo-[c]-cinnolinium chloride.

The 2,9-dichloro-3,8-dimethyl-benzo-[c]-cinnoline is prepared in analogy with the methods of D. Delfs (German Pat. No. 627,138) and J. F. Corbett, P. F. Holt (J. Chem. Soc. 1961, 3698).

EXAMPLE 13

20 ml dimethyl sulphate are added dropwise to a solution of 5 g 2,9-dichloro-3,8-dimethoxy-benzo-[c]-cinnoline in 500 ml chlorobenzene, and the mixture is heated at 100°-120° C. for 8 hours. When the mixture cools down, a brown water-soluble substance crystallises which has the following probable formula

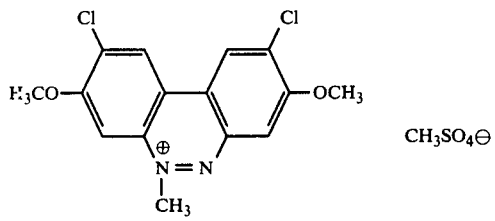

When the dimethyl sulphate is replaced in the above Example with equivalent amounts of diethyl sulphate or benzyl chloride and the quaternisation is carried out in chlorobenzene at 100°–120° C., then there is obtained the likewise water-soluble 2,9-dichloro-3,8-dimethoxy-N-ethyl-benzo-[c]-cinnolinium ethylsulphate or 2,9-dichloro-3,8-dimethoxy-N-benzyl-benzo-[c]-cinnolinium chloride.

The 2,9-dichloro-3,8-dimethoxy-benzo-[c]-cinnoline is synthetised in analogy with the methods of D. Delfs (German Pat. No. 627,138) and J. F. Corbett, P. F. Holt (J. Chem. Soc. 1961, 3698).

EXAMPLE 14

5 g 2,9-dichloro-benzo-[c]-cinnoline-N-oxide are dissolved in 500 ml chlorobenzene, 20 ml dimethyl sulphate are added dropwise, and the mixture is heated at 100°–120° C. for 10 hours. When the mixture cools down, a brown water-soluble substance crystallises which has the following probable formula

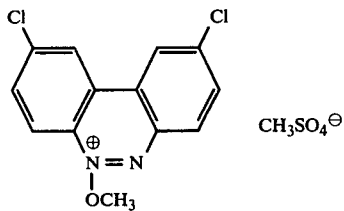

When the dimethyl sulphate is replaced in the above Example with equivalent amounts of diethyl sulphate or benzyl chloride and the quaternisation is carried out in chlorobenzene at 100°–120° C., then there is obtained the likewise water-soluble 2,9-dichloro-N-ethoxy-benzo-[c]-cinnolinium ethylsulphate or 2,9-dichloro-N-benzyloxy-benzo-[c]-cinnolinium chloride.

The 2,9-dichloro-benzo-[c]-cinnoline-N-oxide is prepared according to the processes of J. F. Corbett, P. F. Holt, A. N. Hughes, M. Vickery (J. Chem. Soc. 1962, 1823).

EXAMPLE 15

5 g 2,9-dibromo-benzo-[c]-cinnoline-N-oxide are dissolved in 500 ml chlorobenzene, 20 ml dimethyl sulphate are added dropwise, and the mixture is heated at 100°–120° C. for 10 hours. When the mixture cools down, a brown water-soluble substance crystallises, which has the following probable formula

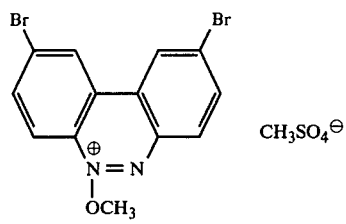

When the dimethyl sulphate is replaced in the above Example with equivalent amounts of diethyl sulphate or benzyl chloride and the quaternisation is carried out in chlorobenzene at 100°–120° C., then there is obtained the likewise water-soluble 2,9-dibromo-N-ethoxy-benzo-[c]-cinnolinium ethylsulphate or 2,9-dibromo-N-benzyloxy-benzo-[c]-cinnolinium chloride.

The 2,9-dibromo-benzo-[c]-cinnoline-N-oxide is prepared in analogy with the process of J. F. Corbett, P. F. Holt, A. N. Hughes, M. Vickery (J. Chem. Soc. 1962, 1823).

EXAMPLE 16

3 g 2-chloro-benzo-[c]-cinnoline-N-oxide are dissolved in 300 ml chlorobenzene, 20 ml dimethyl sulphate are added dropwise, and the mixture is heated at 100°–120° C. for 10 hours. When the mixture cools down, a brown water-soluble substance crystallises, which has the probable formula

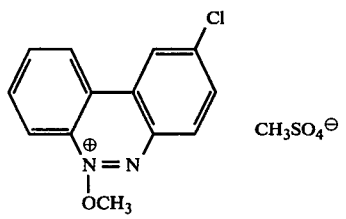

When the dimethyl sulphate is replaced in the above Example with equivalent amounts of diethyl sulphate or benzyl chloride and the quaternisation is carried out in chlorobenzene at 100°–120° C., then there is obtained the likewise water-soluble 2-chloro-N-ethoxy-benzo-[c]-cinnolinium ethylsulphate or 2-chloro-N-benzyloxy-benzo-[c]-cinnolinium chloride.

The 2-chloro-benzo-[c]-cinnoline-N-oxide is prepared in analogy with the process of J. F. Corbett, P. F. Holt (J. Chem. Soc. 1961, 5035).

EXAMPLE 17

3 g 2-bromo-benzo-[c]-cinnoline-N-oxide are dissolved in 300 ml chlorobenzene, 20 ml dimethyl sulphate are added dropwise, and the mixture is heated at 100°–120° C. for 10 hours. When the mixture cools down, a brown water-soluble substance crystallises, which has the following probable formula

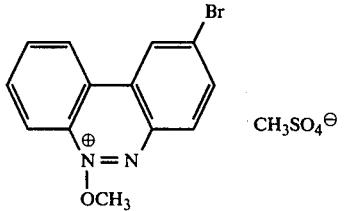

When the dimethyl sulphate is replaced in the above Example with equivalent amounts of diethyl sulphate or benzyl chloride and the quaternisation is carried out in chlorobenzene at 100°-120° C., then there is obtained the likewise water-soluble 2-bromo-N-ethoxy-benzo-[c]-cinnolinium ethylsulphate or 2-bromo-N-benzyloxy-benzo-[c]-cinnolinium chloride.

The 2-bromo-benzo-[c]-cinnoline-N-oxide is prepared according to the process described by J. F. Corbett, P. F. Holt (J. Chem. Soc. 1961, 5035).

EXAMPLE 18

20 ml dimethyl sulphate are added dropwise to a solution of 5 g 2,9-dichloro-3,8-dimethyl-benzo-[c]-cinnoline-N-oxide in 500 ml chlorobenzene, and the mixture is heated at 100°-120° C. for 7 hours. When the mixture cools down, a brown water-soluble substance crystallises, which has the following probable formula

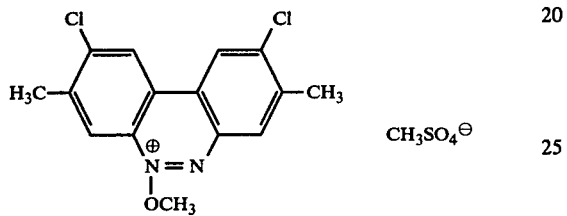

When the dimethyl sulphate is replaced in the above Example with equivalent amounts of diethyl sulphate or benzyl chloride and the quaternisation is carried out in chlorobenzene at 100°-120° C., then there is obtained the likewise water-soluble 2,9-dichloro-3,8-dimethyl-N-ethoxy-benzo-[c]-cinnolinium ethylsulphate or 2,9-dichloro-3,8-dimethyl-N-benzyloxy-benzo-[c]-cinnolinium chloride.

The 2,9-dichloro-3,8-dimethyl-benzo-[c]-cinnoline-N-oxide is prepared in analogy with the methods of D. Delfs (German Patent No. 627,138) and J. F. Corbett et al. (J. Chem. Soc. 1962, 1823).

EXAMPLE 19

20 ml dimethyl sulphate are added to a solution of 5 g 2,9-dichloro-3,8-dimethoxy-benzo-[c]-cinnoline-N-oxide in 500 ml chlorobenzene, and the mixture is heated at 100°-120° C. for 8 hours. When the mixture has cooled down, a brown water-soluble substance crystallises, which has the probable formula

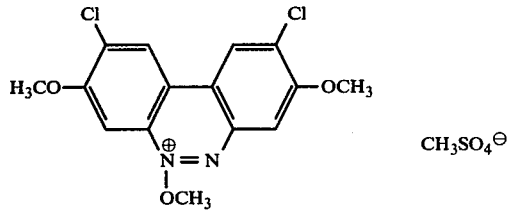

When the dimethyl sulphate is replaced in the above Example with equivalent amounts of diethyl sulphate or benzyl chloride and the quaternisation is carried out in chlorobenzene at 100°-120° C., then there is obtained the likewise watersoluble 2,9-dichloro-3,8-dimethoxy-N-ethoxy-benzo-[c]-cinnolinium ethylsulphate or 2,9-dichloro-3,8-dimethoxy-N-benzyloxy-benzo-[c]-cinnolinium chloride.

The 2,9-dichloro-3,8-dimethoxy-benzo-[c]-cinnolinium-N-oxide is prepared in analogy with the methods of D. Delfs (German Pat. No. 627,138) and J. F. Corbett et al. (J. Chem. Soc. 1962, 1823).

EXAMPLE 20

2 g aniline in 30 ml alcohol are added dropwise to a solution of 4.6 g 2,9-dibromo-N-methyl-benzo-[c]-cinnolinium methosulphate in 80 ml of water. The mixture is stirred at room temperature for 3 hours and then heated under reflux for 1 hour.

When the mixture cools down, dark red crystals are precipitated, which are a red powder when dried and dissolve in water with a red colour. The dyestuff cation of the probable formula

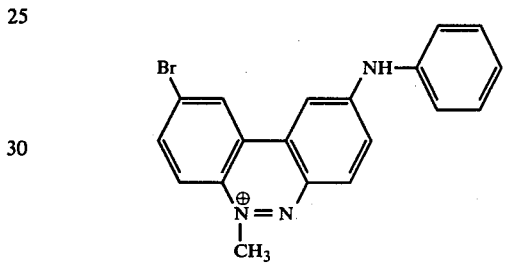

has methosulphate and bromide as anions.

The dyestuff dyes materials of polyacrylonitrile in red shades. It can be converted into the other anions described in Example 1. The same shade is obtained with these anions on polyacrylonitrile.

When the cationic starting compound is replaced in the above Example with equivalent amounts of 2,9-dibromo-N-benzyl-benzo[c]-cinnolinium chloride or 2,9-dibromo-N-ethyl-benzo-[c]-cinnolinium ethylsulphate and the condensation with aniline is carried out as described, then red dyestuffs are again obtained, which dye materials of polyacrylonitrile in red shades.

When the aniline is replaced in the above Example with equivalent amounts of the amines listed in Column 1 of the following Table, then cationic dyestuffs are likewise obtained, which have the shades specified in Column 2.

| Column 1 Amine | Column 2 Shade on Polyacrylonitrile |
|---|---|
| methylamine | orange |
| dimethylamine | orange |
| diethylamine | orange |
| cyanoethylamine | orange |
| ethanolamine | orange |
| diethanolamine | red-orange |
| iso-propylamine | red-orange |
| n-butylamine | yellowish red |

-continued

| Column 1<br>Amine | Column 2<br>Shade on Polyacrylonitrile |
|---|---|
| ethylene-diamine | orange |
| 3-amino-1-dimethylamino-propane | red-orange |
| aniline | red |
| 4-ethoxy-aniline | Bordeaux |
| 4-dimethylamino-aniline | brown-violet |
| 2-chloro-aniline | brown-red |
| 3-chloro-aniline | red |
| 4-chloro-aniline | yellowish red |
| 3-nitro-aniline | red-brown |
| 4-nitro-aniline | red-brown |
| 2,4-dinitro-aniline | red-brown |
| o-toluidine | yellowish red |
| n-dodecylamine | orange |
| morpholine | orange |
| piperazine | orange |
| cyclohexylamine | red-orange |
| N-methyl-cyclohexylamine | red-orange |
| hydrazine | orange |
| N,N-dimethylhydrazine | orange |
| phenylhydrazine | red |
| semicarbazide | yellowish red |
| o-anisidine | red |
| m-anisidine | red |
| p-anisidine | bluish red |
| m-toluidine | bluish red |
| p-toluidine | red |
| o-phenylene-diamine | red-brown |
| m-phenylene-diamine | red |
| p-phenylene-diamine | violet |
| benzidine | violet |
| N-acetyl-p-phenylene-diamine | red |
| 2-amino-4-acetylamino-anisole | red |
| α-naphthylamine | brown-red |
| 1,5-diamino-naphthalene | red-brown |
| 4-amino-phenyl | bluish red |
| anthranilic acid methyl ester | red-brown |
| 4-amino-benzoic acid methyl ester | red |
| 4-amino-azobenzene | red-brown |
| 4-amino-diphenylamine | black |
| 2,4-dimethoxy-aniline | red |
| N-methyl-aniline | red |
| N-ethyl-m-toluidine | orange-red |
| 4,4'-diamino-diphenyl ether | bluish red |
| 4-amino-4'-methoxy-diphenylamine | black |
| benzylamine | brown-red |
| 2-methyl-dihydro-(2,3)-indole | violet |
| 2-amino-benzothiazole | orange-red |
| 3-amino-1,2,4-triazole | red-orange |
| imidazole | orange |
| 1,2,3,4-tetrahydroquinoline | brown |
| 2-amino-pyridine | orange |
| 3-amino-pyridine | orange |
| 4-amino-pyridine-N-oxide | yellow |
| piperidine | yellow-orange |
| pyrrolidine | red-orange |
| 3-phenyl-pyrazoline-($\Delta$ 2) | red |
| 3-4'-methylphenyl-pyrazoline-($\Delta$ 2) | red |
| 3-4'ethylphenyl-pyrazoline-($\Delta$ 2) | red |
| 3-3'-methylphenyl-pyrazoline-($\Delta$ 2) | red |
| 3-4'-methylsulphonyl-pyrazoline-($\Delta$ 2) | |
| 3-4'-methoxyphenyl-pyrazoline-($\Delta$ 2) | red |
| 3-4'-ethoxyphenyl-pyrazoline-($\Delta$ 2) | red |
| 3-4'-n-butoxyphenyl-pyrazoline-($\Delta$ 2) | red |
| 3-4'-iso-amyloxyphenyl-pyrazoline-($\Delta$ 2) | red |
| 3-4'-trifluorophenyl-pyrazoline-($\Delta$ 2) | red |
| 3-4'-fluorophenyl-pyrazoline-($\Delta$ 2) | red |
| 3-4'-chlorophenyl-pyrazoline-($\Delta$ 2) | red |
| 3-4'-bromophenyl-pyrazoline-($\Delta$ 2) | red |
| 3-4'-cyanophenyl-pyrazoline-($\Delta$ 2) | red |
| 3-4'-($\beta$-diethylaminoethoxy)-phenyl-pyrazoline-($\Delta$ 2) | red |
| 3-4'-α-thienyl-pyrazoline-$\Delta$ 2) | red |
| 3-4'-biphenylyl-pyrazoline-($\Delta$ 2) | red |
| 3-3',5'-dimethylphenyl-pyrazoline-($\Delta$ ) | red |
| 3-3',4'-dimethoxyphenyl-pyrazoline-($\Delta$ ) | red |
| 3-styryl-5-phenyl-pyrazoline-($\Delta$ 2) | red |
| 3-4'-chlorostyryl-4-4'-chlorophenyl-pyrazoline-($\Delta$ 2) | red |
| 3,4-diphenyl-pyrazoline-($\Delta$2) | red |
| 3,5-diphenyl-pyrazoline-($\Delta$ 2) | red |
| 3-phenyl-5,5-dimethyl-pyrazoline-($\Delta$ 2) | red |
| 3-phenyl-4,4-dimethyl-pyrazoline-($\Delta$ 2) | red |

EXAMPLE 21

2 g aniline in 30 ml alcohol are added dropwise to a solution of 3.9 g 2-bromo-N-methyl-benzo-[c]-cinnolinium methosulphate in 80 ml of water. The mixture is stirred at room temperature for 3 hours and then heated under reflux for 1 hour. When the mixture cools down, dark red crystals are precipitated, which dissolve in water with a red colour.

The dyestuff cation of the probable formula

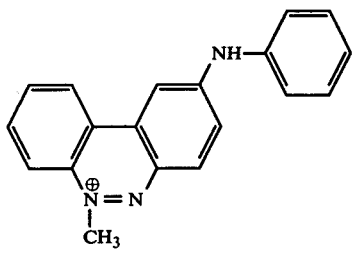

has methosulphate and bromide as anions.

The dyestuff dyes materials of polyacrylonitrile in red shades. It can be converted into the other anions described in Example 1.

When the cationic starting compound is replaced in the above Example with 2-chloro-N-methyl-benzo-[c]-cinnolinium methosulphate, the same dyestuff cation is obtained. When in this Ex. the cationic starting compound is replaced with 2-chloro- (or 2-bromo)-N-benzyl-benzo-[c]-cinnolinium chloride or with 2-chloro- (or 2-bromo)-N-ethyl-benzo-[c]-cinnolinium ethylsulphate, then there are again obtained dyestuffs which dye materials of polyacrylonitrile in red shades.

When the aniline is replaced in the above Example with equivalent amounts of the amines listed in Column 1 of the following Table, then cationic dyestuffs are likewise obtained, which have the shades specified in Column 2.

| Colume 1 Amine | Column 2 Shade on Polyacrylonitrile |
|---|---|
| methylamine | orange |
| dimethylamine | orange |
| diethylamine | orange |
| cyanoethylamine | orange |
| ethanolamine | orange |
| diethanolamine | red-orange |
| iso-propylamine | red-orange |
| n-butylamine | yellowish red |
| ethylene-diamine | orange |
| 3-amino-1-dimethylamino-propane | red-orange |
| aniline | red |
| 4-ethoxy-aniline | Bordeaux |
| 4-dimethylamino-aniline | brown-violet |
| 2-chloro-aniline | brown-red |
| 3-chloro-aniline | red |
| 4-chloro-aniline | yellowish red |
| 3-nitro-aniline | red-brown |
| 4-nitro-aniline | red-brown |
| 2,4-dinitro-aniline | red-brown |
| o-toluidine | yellowish red |
| n-dodecylamine | orange |
| morpholine | orange |
| piperazine | orange |
| cyclohexylamine | red-orange |
| N-methyl-cyclohexylamine | red-orange |
| hydrazine | orange |
| N,N-dimethylhydrazine | orange |
| phenylhydrazine | red |
| semicarbazide | yellowish red |
| o-anisidine | red |
| m-anisidine | red |
| p-anisidine | bluish red |
| m-toluidine | bluish red |
| p-toluidine | red |
| o-phenylene-diamine | red-brown |
| m-phenylene-diamine | red |
| p-phenylene-diamine | violet |
| benzidine | violet |
| N-acetyl-p-phenylene-diamine | red |
| 2-amino-4-acetylamino-anisole | red |
| α-naphthylamine | brown-red |
| 1,5-diamino-naphthalene | red-brown |
| 4-amino-phenyl | bluish red |
| anthranilic acid methyl ester | red-brown |
| 4-amino-benzoic acid methyl ester | red |
| 4-amino-azobenzene | red-brown |
| 4-amino-diphenylamine | black |
| 2,4-dimethoxy-aniline | red |
| N-methyl-aniline | red |
| N-ethyl-m-toluidine | orange-red |
| 4,4'-diamino-diphenyl ether | bluish red |
| 4-amino-4'-methoxy-diphenylamine | black |
| benzylamine | brown-red |
| 2-methyl-dihydro-(2,3)-indole | violet |
| 2-amino-benzothiazole | orange-red |
| 3-amino-1,2,4-triazole | red-orange |
| imidazole | orange |
| 1,2,3,4-tetrahydroquinoline | brown |
| 2-amino-pyridine | orange |
| 3-amino-pyridine | orange |
| 4-amino-pyridine-N-oxide | yellow |
| piperidine | yellow-orange |
| pyrrolidine | red-orange |
| 3-phenyl-pyrazoline-(Δ 2) | red |
| 3-4'-methylphenyl-pyrazoline-(Δ 2) | red |
| 3-4'ethylphenyl-pyrazoline-(Δ 2) | red |
| 3-3'-methylphenyl-pyrazoline-(Δ 2) | red |
| 3-4'-methylsulphonyl-pyrazoline-(Δ 2) | |
| 3-4'-methoxyphenyl-pyrazoline-(Δ 2) | red |
| 3-4'-ethoxyphenyl-pyrazoline-(Δ 2) | red |
| 3-4'-n-butoxyphenyl-pyrazoline-(Δ 2) | red |
| 3-4'-iso-amyloxyphenyl-pyrazoline-(Δ 2) | red |
| 3-4'-trifluorophenyl-pyrazoline-(Δ 2) | red |
| 3-4'-fluorophenyl-pyrazoline-(Δ 2) | red |
| 3-4'-chlorophenyl-pyrazoline-(Δ 2) | red |
| 3-4'-bromophenyl-pyrazoline-(Δ 2) | red |
| 3-4'-cyanophenyl-pyrazoline-(Δ 2) | red |
| 3-4'-(β-diethylaminoethoxy)-phenyl-pyrazoline-(Δ 2) | red |
| 3-4'-α-thienyl-pyrazoline-(Δ2) | red |
| 3-4'-diphenylyl-pyrazoline-(Δ 2) | red |
| 3-3',5'-dimethylphenyl-pyrazoline-(Δ) | red |
| 3-3',4'-dimethoxyphenyl-pyrazoline-(Δ) | red |
| 3-styryl-5-phenyl-pyrazoline-(Δ 2) | red |
| 3-4'-chlorostyryl-4-4'-chlorophenyl-pyrazoline-(Δ 2) | red |
| 3,4-diphenyl-pyrazoline-(Δ2) | red |
| 3,5-diphenyl-pyrazoline-(Δ 2) | red |
| 3-phenyl-5,5-dimethyl-pyrazoline-(Δ 2) | red |
| 3-phenyl-4,4-dimethyl-pyrazoline-(Δ 2) | red |

EXAMPLE 22

2 g aniline in 30 ml alcohol are added dropwise to a solution of 4 g 2,9-dichloro-3,8-dimethyl-N-methyl-benzo-[c]-cinnolinium methosulphate in 80 ml of water. A red dyestuff is formed. The mixture is stirred at room temperature for 2 hours and then heated under reflux for 1 hour. When the mixture cools down, dark red crystals are precipitated, which dissolve in water with a red colour.

The dyestuff cation of the probable formula

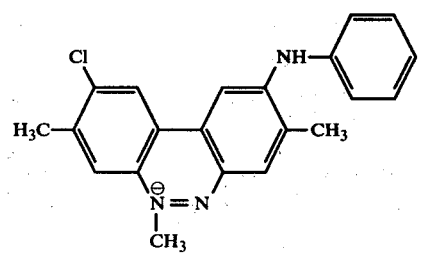

has methosulphate and chloride as anions.

The dyestuff dyes materials of polyacrylonitrile in red shades. It can be converted into the other anions described in Example 1. The dyestuff has the same shade with these anions.

When the cationic starting compound is replaced in the above Example with equivalent amounts of 2,9-dichloro-3,8-dimethyl-N-ethyl-benzo-[c]-cinnolinium ethylsulphate or 2,9-dichloro-3,8-dimethyl-N-benzyl-benzo-[c]-cinnolinium chloride and the condensation is carried out with aniline as described, then dyestuffs are again obtained, which dye materials of polyacrylonitrile in red shades.

When the aniline is replaced in the above Example with equivalent amounts of the amines listed in Column 1 of the following Table, then cationic dyestuffs are likewise obtained, which have the shades specified in Column 2.

| Column 1<br>Amine | Column 2<br>Shade<br>on Polyacrylonitrile |
|---|---|
| methylamine | orange |
| dimethylamine | " |
| diethylamine | " |
| cyanoethylamine | " |
| ethanolamine | - |
| diethanolamine | red-orange |
| iso-propylamine | " |
| n-butylamine | yellowish red |
| ethylene-diamine | orange |
| 3-amino-1-dimethylamino-propane | red-orange |
| aniline | red |
| 4-ethoxy-aniline | Bordeaux |
| 4-dimethylamino-aniline | brown-violet |
| 2-chloro-aniline | brown-red |
| 3-chloro-aniline | red |
| 4-chloro-aniline | yellowish red |
| 3-nitro-aniline | red-brown |
| 4-nitro-aniline | " |
| 2,4-dinitro-aniline | " |
| o-toluidine | yellowish red |
| n-dodecylamine | orange |
| morpholine | " |
| piperazine | " |
| cyclohexylamine | red-orange |
| N-methyl-cyclohexylamine | " |
| hydrazine | orange |
| N,N-dimethylhydrazine | " |
| phenylhydrazine | red |
| semicarbazide | yellowish red |
| o-anisidine | red |
| m-anisidine | red |
| p-anisidine | bluish red |
| m-toluidine | " |
| p-toluidine | red |
| o-phenylene-diamine | red-brown |
| m-phenylene-diamine | red |
| p-phenylene-diamine | violet |
| benzidine | " |
| N-acetyl-p-phenylene-diamine | red |
| 2-amino-4-acetylamino-anisole | " |
| α-naphthylamine | brown-red |
| 1,5-diamino-naphthalene | red-brown |
| 4-amino-phenol | bluish red |
| anthranilic acid methyl ester | red-brown |
| 4-amino-benzoic acid methyl ester | red |
| 4-amino-azobenzene | red-brown |
| 4-amino-diphenylamine | black |
| 2,4-dimethoxy-aniline | red |
| N-methyl-aniline | " |
| N-ethyl-m-toluidine | orange-red |
| 4,4'-diamino-diphenyl ether | bluish red |
| 4-amino-4'-methoxy-diphenylamine | black |
| benzylamine | brown-red |
| 2-methyl-dihydro-(2,3)-indole | violet |
| 2-amino-benzothiazole | orange-red |
| 3-amino-1,2,4-triazole | red-orange |
| imidazole | orange |
| 1,2,3,4-tetrahydroquinoline | brown |
| 2-amino-pyridine | orange |
| 3-amino-pyridine | " |
| 4-amino-pyridine-N-oxide | yellow |
| piperidine | yellow-orange |
| pyrrolidine | red-orange |
| 3-phenyl-pyrazoline-(Δ2) | red |
| 3-4'-methylphenyl-pyrazoline-(Δ2) | " |
| 3-4'-ethylphenyl-pyrazoline-(Δ2) | " |
| 3-3'-methylphenyl-pyrazoline-(Δ2) | " |
| 3-4'-methylsulphonyl-pyrazoline-(Δ2) | " |
| 3-4'-methoxyphenyl-pyrazoline-(Δ2) | " |

-continued

| Column 1<br>Amine | Column 2<br>Shade<br>on Polyacrylonitrile |
|---|---|
| 3-4'-ethoxyphenyl-pyrazoline-(Δ2) | " |
| 3-4'-n-butoxyphenyl-pyrazoline-(Δ2) | " |
| 3-4'-iso-amyloxyphenyl-pyrazoline-(Δ2) | " |
| 3-4'-trifluorophenyl-pyrazoline-(Δ2) | " |
| 3-4'-fluorophenyl-pyrazoline-(Δ2) | " |
| 3-4'-chlorophenyl-pyrazoline-(Δ2) | " |
| 3-4'-bromophenyl-pyrazoline-(Δ2) | " |
| 3-4'-cyanophenyl-pyrazoline-(Δ2) | " |
| 3-4'-(β-diethylaminoethoxy)-phenyl-pyrazoline-(Δ2) | " |
| 3-4'-α-thienyl-pyrazoline-(Δ2) | " |
| 3-4'-biphenylyl-pyrazoline-(Δ2) | " |
| 3-3',5'-dimethylphenyl-pyrazoline-(Δ2) | " |
| 3-3',4'-dimethoxyphenyl-pyrazoline-(Δ2) | " |
| 3-styryl-5-phenyl-pyrazoline-(Δ2) | " |
| 3-4'-chlorostyryl-4-4'-chlorophenyl-pyrazoline-(Δ2) | " |
| 3,4-diphenyl-pyrazoline-(Δ2) | " |
| 3,5-diphenyl-pyrazoline-(Δ2) | " |
| 3-phenyl-5,5-dimethyl-pyrazoline-(Δ2) | " |
| 3-phenyl-4,4-dimethyl-pyrazoline-(Δ2) | " |

EXAMPLE 23

2 g aniline in 30 ml alcohol are added dropwise to a solution of 4.4 g 2,9-dichloro-3,8-dimethoxy-N-methyl-benzo-[c]-cinnolinium methosulphate in 80 ml of water. A bluish red dyestuff is formed. The mixture is stirred at room temperature for 2 hours and then heated under reflux for 1 hour. When the mixture cools down, a dyestuff is precipitated, which dissolves in water with a bluish red colour.

The dyestuff cation of the probable formula has methosulphate and chloride as anions.

The dyestuff dyes materials of polyacrylonitrile in bluish red shades. It can be converted into the other anions described in Example 1. The dyestuff has the same shade on polyacrylonitrile with these anions.

When the cationic starting compound is replaced in the above Example with equivalent amounts of 2,9-dichloro-3,8-dimethoxy-N-ethyl-benzo-[c]-cinnolinium ethylsulphate or 2,9-dichloro-3,8-dimethoxy-N-benzyl-benzo-[c]-cinnolinium chloride and the condensation is carried out with aniline as described, then dyestuffs are again obtained, which dye materials of polyacrylonitrile in bluish red shades.

When the aniline is replaced in the above Example with equivalent amounts of the amines listed in Column 1 of the following Table, then cationic dyestuffs are likewise obtained, which have the shades specified in Column 2.

| Column 1 Amine | Column 2 Shade on Polyacrylonitrile |
|---|---|
| methylamine | orange |
| dimethylamine | " |
| diethylamine | " |
| cyanoethylamine | " |
| ethanolamine | " |
| diethanolamine | red-orange |
| isopropylamine | " |
| n-butylamine | red |
| ethylene-diamine | orange |
| 3-amino-1-dimethylamino-propane | red |
| n-dodecylamine | orange |
| aniline | bluish red |
| 4-ethoxy-aniline | violet |
| 4-dimethylamino-aniline | " |
| 2-chloro-aniline | red |
| 3-chloro-aniline | " |
| 4-chloro-aniline | " |
| 3-nitro-aniline | " |
| 4-nitro-aniline | " |
| 2,4-dinitro-aniline | " |
| o-toluidine | " |
| m-toluidine | bluish red |
| p-toluidine | " |
| o-phenylene-diamine | red |
| m-phenylene-diamine | bluish red |
| p-phenylene-diamine | violet |
| benzidine | blue-violet |
| N-acetyl-p-phenylene-diamine | bluish red |
| 2-amino-4-acetylamino-anisole | " |
| α-naphthylamine | red |
| 1,5-diamino-naphthalene | red |
| 4-amino-phenol | violet |
| anthranilic acid methyl ester | red |
| 4-amino-benzoic acid methyl ester | bluish red |
| 4-amino-azobenzene | red |
| 4-amino-diphenylamine | black |
| 2,4-dimethoxy-aniline | bluish red |
| N-methylaniline | " |
| N-ethyl-m-toluidine | red |
| 4,4-diamino-diphenyl ether | violet |
| 4-amino-4-methoxy-diphenylamine | black |
| benzylamine | red |
| 2-methyl-dihydro-(2,3)-indole | violet |
| 2-amino-benzothiazole | bluish red |
| 3-amino-1,2,4-triazole | red |
| imidazole | " |
| 1,2,3,4-tetrahydroquinoline | " |
| 2-amino-pyridine | " |
| 3-amino-pyridine | " |
| 4-amino-pyridine-N-oxide | orange |
| piperidine | " |
| pyrrolidine | red-orange |
| morpholine | orange-red |
| piperazine | " |
| cyclohexylamine | " |
| N-methylamine | " |
| hydrazine | orange |
| N,N-dimethylhydrazine | orange-red |
| phenylhydrazine | bluish red |
| semicarbaside | red |
| o-anisidine | bluish red |
| m-anisidine | " |
| p-anisidine | " |
| 3-phenyl-pyrazoline-(Δ2) | " |
| 3-4'-methylphenyl-pyrazoline-(Δ2) | " |
| 3-4'-ethylphenyl-pyrazoline-(Δ2) | " |
| 3-3'-methylphenyl-pyrazoline-(Δ2) | " |
| 3-4'-methylsulphonyl-pyrazoline-(Δ2) | " |
| 3-4'-methoxyphenyl-pyrazoline-(Δ2) | " |
| 3-4'-ethoxyphenyl-pyrazoline-(Δ2) | " |
| 3-4'-n-butoxyphenyl-pyrazoline-(Δ2) | " |
| 3-4'-iso-amyloxyphenyl-pyrazoline-(Δ2) | " |
| 3-4'-trifluorophenyl-pyrazoline-(Δ2) | " |
| 3-4'-fluorophenyl-pyrazoline-(Δ2) | " |
| 3-4'-chlorophenyl-pyrazoline-(Δ2) | " |
| 3-4'-bromophenyl-pyrazoline-(Δ2) | " |
| 3-4'-cyanophenyl-pyrazoline-(Δ2) | " |
| 3-4'-(β-diethylaminoethoxy)-phenyl-pyrazoline-(Δ2) | " |
| 3-4'-α-thienyl-pyrazoline-(Δ2) | " |
| 3-4'-biphenylyl-pyrazoline-(Δ2) | " |
| 3-3',5'-dimethylphenyl-pyrazoline-(Δ2) | " |
| 3-3',4'-dimethoxyphenyl-pyrazoline-(Δ2) | " |
| 3-styryl-5-phenyl-pyrazoline-(Δ2) | " |
| 3-4'-chlorostyryl-4-4'-chlorophenyl-pyrazoline-(Δ2) | " |
| 3,4-diphenyl-pyrazoline-(Δ2) | " |
| 3,5-diphenyl-pyrazoline-(Δ2) | " |
| 3-phenyl-5,5-dimethyl-pyrazoline-(Δ2) | " |

-continued

| Column 1 Amine | Column 2 Shade on Polyacrylonitrile |
|---|---|
| 3-phenyl-4,4-dimethyl-pyrazoline-(Δ2) | " |

EXAMPLE 24

2 g aniline in 30 ml alcohol are added dropwise to a solution of 3.9 g 2,9-dichloro-N-methoxy-benzo-[c]-cinnolinium methosulphate in 60 ml of water. The mixture is stirred at room temperature for 2 hours and subsequently heated under reflux for 1 hour. When the mixture cools down, a red dyestuff is precipitated, which dissolves in water with a red colour.

The dyestuff cation of the probable formula

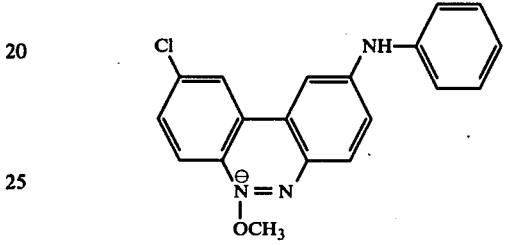

has methosulphate and chloride as anions.

The dyestuff dyes materials of polyacrylonitrile in yellowish red shades. It can be converted into the other anions described in Example 1. The dyestuff has the same shades on polyacrylonitrile with these anions.

When the cationic starting compound is replaced in the above Example with equivalent amounts of 2,9-dichloro-N-ethoxy-benzo-[c]-cinnolinium ethylsulphate or 2,9-dichloro-N-benzyloxy-benzo-[c]-cinnolinium chloride and the condensation is carried out with aniline as described, then dyestuffs are again obtained which dye materials of polyacrylonitrile in yellowish red shades.

When the aniline is replaced in the above Example with equivalent amounts of the amines listed in Column 1 of the following Table, then cationic dyestuffs are likewise obtained, which have the shades specified in Column 2.

| Amine | Shade on Polyacrylonitrile |
|---|---|
| aniline | yellowish red |
| o-toluidine | orange |
| m-toluidine | red-orange |
| 4-chloro-aniline | orange |
| p-phenylene-diamine | violet |
| N-acetyl-p-phenylene-diamine | red |
| 4,4'-diamino-diphenyl ether | orange |
| 4-amino-diphenylamine | violet |
| 4-amino-4'-methoxy-diphenylamine | " |
| anthranilic acid methyl ester | red-orange |
| 2-methyl-dihydro-indole | violet |
| pyrrolidine | orange |
| morpholine | " |
| phenylhydrazine | " |
| benzidine | violet |
| o-anisidine | yellowish red |
| m-anidine | " |
| p-anisidine | red |
| 3-phenyl-pyrazoline-(Δ2) | yellowish red |
| 3-4'-methylphenyl-pyrazoline-(Δ2) | " |
| 3-4'-ethylphenyl-pyrazoline-(Δ2) | " |
| 3-3'-methylphenyl-pyrazoline-(Δ2) | " |
| 3-4'-methylsulphonyl-pyrazoline-(Δ2) | " |
| 3-4'-methoxyphenyl-pyrazoline-(Δ2) | " |
| 3-4'-ethoxyphenyl-pyrazoline-(Δ2) | " |
| 3-4'-α-butoxyphenyl-pyrazoline-(Δ2) | " |

-continued

| Amine | Shade on Polyacrylonitrile |
|---|---|
| 3-4'-iso-amyloxyphenyl-pyrazoline-(Δ2) | " |
| 3-4'-trifluorophenyl-pyrazoline-(Δ2) | " |
| 3-4'-fluorophenyl-pyrazoline-(Δ2) | " |
| 3-4'-chlorophenyl-pyrazoline-(Δ2) | " |
| 3-4'-bromophenyl-pyrazoline-(Δ2) | yellowish red |
| 3-4'-cyanophenyl-pyrazoline-(Δ2) | " |
| 3-4'-(β-diethylaminoethoxy)-phenyl-pyrazoline-(Δ2) | " |
| 3-4'-α-thienyl-pyrazoline-(Δ2) | " |
| 3-4'-biphenylyl-pyrazoline-(Δ2) | " |
| 3-3',5'-dimethylphenyl-pyrazoline-(Δ2) | " |
| 3-3',4'-dimethoxyphenyl-pyrazoline-(Δ2) | " |
| 3-styryl-5-phenyl-pyrazoline-(Δ2) | " |
| 3-4'-chlorostyryl-4-4'-chlorophenyl-pyrazoline-(Δ2) | " |
| 3,4-diphenyl-pyrazoline-(Δ2) | " |
| 3,5-diphenyl-pyrazoline-(Δ2) | " |
| 3-phenyl-5,5-dimethyl-pyrazoline-(Δ2) | " |
| 3-phenyl-4,4-dimethyl-pyrazoline-(Δ2) | " |

EXAMPLE 25

2 g aniline in 30 ml alcohol are added dropwise to a solution of 4.8 g 2,9-dibromo-N-methoxy-benzo-[c]-cinnolinium methosulphate in 80 ml of water. The mixture is stirred at room temperature for 2 hours and then heated under reflux for 1 hour. When the mixture cools down, a dyestuff is precipitated which dissolves in water with a red colour.

The dyestuff cation of the probable formula

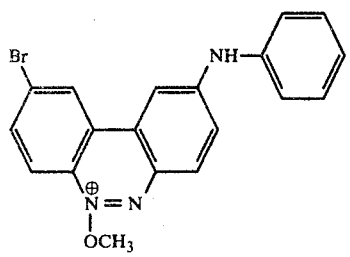

has methosulphate and bromide as anions.

The dyestuff dyes materials of polyacrylonitrile in yellowish red shades. It can be converted into the other anions described in Example 1. The dyestuff has the same shades on polyacrylonitrile with these anions.

When the cationic starting compound is replaced in the above Example with equivalent amounts of 2,9-dibromo-N-ethoxy-benzo-[c]-cinnolinium ethylsulphate or 2,9-dibromo-N-benzyloxy-benzo-[c]-cinnolinium chloride and the condensation is carried out with aniline as described, then dyestuffs are again obtained, which dye materials of polyacrylonitrile in yellowish-red shades.

When the aniline is replaced in the above Example with equivalent amounts of the amines listed in Column 1 of the following Table, then cationic dyestuffs are likewise obtained, which have the shades specified in Column 2.

| Amine | Shade on Polyacrylonitrile |
|---|---|
| aniline | yellowish red |
| o-toluidine | orange |
| m-toluidine | red-orange |
| 4-chloro-aniline | orange |
| p-phenylene-diamine | violet |
| N-acetyl-p-phenylene-diamine | red |
| 4,4'-diamino-diphenyl ether | orange |
| 4-amino-diphenylamine | violet |
| 4-amino-4'-methoxy-diphenylamine | " |
| anthranilic acid methyl ester | red-orange |
| 2-methyl-dihydro-indole | violet |
| pyrrolidine | orange |
| morpholine | " |
| phenylhydrazine | " |
| benzidine | violet |
| o-anisidine | yellowish red |
| m-anisidine | yellowish red |
| p-" | red |
| 3-phenyl-pyrazoline-(Δ2) | yellowish red |
| 3-4'-methylphenyl-pyrazoline-(Δ2) | " |
| 3-4'-ethylphenyl-pyrazoline-(Δ2) | " |
| 3-3'-methylphenyl-pyrazoline-(Δ2) | " |
| 3-4'-methylsulphonyl-pyrazoline-(Δ2) | " |
| 3-4'-methoxyphenyl-pyrazoline-(Δ2) | " |
| 3-4'-ethoxyphenyl-pyrazoline-(Δ2) | " |
| 3-4'-n-butoxyphenyl-pyrazoline-(Δ2) | " |
| 3-4'-iso-amyloxyphenyl-pyrazoline-(Δ2) | " |
| 3-4'-trifluorophenyl-pyrazoline-(Δ2) | " |
| 3-4'-fluorophenyl-pyrazoline-(Δ2) | " |
| 3-4'-chlorophenyl-pyrazoline-(Δ2) | " |
| 3-4'-bromophenyl-pyrazoline-(Δ2) | " |
| 3-4'-cyanophenyl-pyrazoline-(Δ2) | " |
| 3-4'-(β-diethylaminoethoxy)-phenyl-pyrazoline-(Δ2) | " |
| 3-4'-α-thienyl-pyrazoline-(Δ2) | " |
| 3-4'-biphenyl-pyrazoline-(Δ2) | " |
| 3-3',5'-dimethylphenyl-pyrazoline-(Δ2) | " |
| 3-3',4'-dimethoxyphenyl-pyrazoline-(Δ2) | " |
| 3-styryl-5-phenyl-pyrazoline-(Δ2) | " |
| 3-4'-chlorostyryl-4-4'-chlorophenyl-pyrazoline-(Δ2) | " |
| 3,4-diphenyl-pyrazoline-(Δ2) | " |
| 3,5-diphenyl-pyrazoline-(Δ2) | " |
| 3-phenyl-5,5-dimethyl-pyrazoline-(Δ2) | " |
| 3-phenyl-4,4-dimethyl-pyrazoline-(Δ2) | " |

EXAMPLE 26

2 g aniline in 30 ml alcohol are added dropwise to a solution of 4.2 g 2,9-dichloro-3,8-dimethyl-N-methoxy-benzo-[c]-cinnolinium methosulphate in 80 ml of water. The mixture is stirred at room temperature for 2 hours and then heated under reflux for 1 hour. When the mixture cools down, a dyestuff is precipitated which dissolves in water with a red colour.

The dyestuff cation of the probable formula

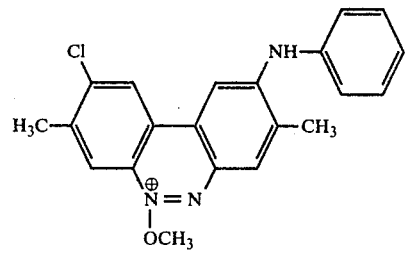

has methosulphate and chloride as anions.

The dyestuff dyes materials of polyacrylonitrile in yellowish red shades. It can be converted into the other anions described in Example 1. The dyestuff has the same shade on polyacrylonitrile with these anions.

When the cationic starting compound is replaced in the above Example with equivalent amounts of 2,9-dichloro-3,8-dimethyl-N-ethoxy-benzo-[c]-cinnolinium ethylsulphate or 2,9-dichloro-3,8-dimethyl-N-benzyloxy-benzo-[c]-cinnolinium chloride, then dyestuffs are again obtained, which dye materials of polyacrylonitrile in yellowish-red shades.

When the aniline is replaced in the above Example with equivalent amounts of the amines listed in Column 1 of the following Table, then cationic dyestuffs are likewise obtained, which have the shades specified in Column 2.

| Amine | Shade on Polyacrylonitrile |
|---|---|
| aniline | yellowish red |
| o-toluidine | orange |
| m-toluidine | red-orange |
| 4-chloro-aniline | orange |
| p-phenylene-diamine | violet |
| N-acetyl-p-phenylene-diamine | red |
| 4,4'-diamino-diphenyl ether | orange |
| 4-amino-diphenylamine | violet |
| 4-amino-4'-methoxy-diphenylamine | " |
| anthranilic acid methyl ester | red-orange |
| 2-methyl-dihydro-indole | violet |
| pyrrolidine | orange |
| morpholine | " |
| phenylhydrazine | " |
| benzidine | violet |
| o-anisidine | yellowish red |
| m-" | yellowish red |
| p-" | red |
| 3-phenyl-pyrazoline-( 2) | yellowish red |
| 3-4'-methylphenyl-pyrazoline-( 2) | yellowish red |
| 3-4'-ethylphenyl-pyrazoline-( 2) | yellowish red |
| 3-3'-methylphenyl-pyrazoline-( 2) | yellowish red |
| 3-4'-methylsulphonyl-pyrazoline-( 2) | yellowish red |
| 3-4'-methoxyphenyl-pyrazoline-( 2) | yellowish red |
| 3-4'-ethoxyphenyl-pyrazoline-( 2) | yellowish red |
| 3-4'-n-butoxyphenyl-pyrazoline-( 2) | yellowish red |
| 3-4'-iso-anyloxyphenyl-pyrazoline-( 2) | yellowish red |
| 3-4'-trifluorophenyl-pyrazoline-( 2) | yellowish red |
| 3-4'-fluorophenyl-pyrazoline-( 2) | yellowish red |
| 3-4'-chlorophenyl-pyrazoline-( 2) | yellowish red |
| 3-4'-bromophenyl-pyrazoline-( 2) | yellowish red |
| 3-4'-cyanophenyl-pyrazoline-( 2) | yellowish red |
| 3-4'-(β-diethylaminoethoxy)-phenyl-pyrazoline-( 2) | yellowish red |
| 3-4'-α-thienyl-pyrazoline-( 2) | yellowish red |
| 3-4'-biphenylyl-pyrazoline-( 2) | yellowish red |
| 3-3',5'-dimethylphenyl-pyrazoline-( 2) | yellowish red |
| 3-3',4'-dimethoxyphenyl-pyrazoline-( 2) | yellowish red |
| 3-styryl-5-phenyl-pyrazoline-( 2) | yellowish red |
| 3-4'-chlorostyryl-4-4'-chlorophenyl-pyrazoline-( 2) | yellowish red |
| 3,4-diphenyl-pyrazoline-( 2) | yellowish red |
| 3,5-diphenyl-pyrazoline-( 2) | yellowish red |
| 3-phenyl-5,5-dimethyl-pyrazoline-( 2) | yellowish red |
| 3-phenyl-4,4-dimethyl-pyrazoline-( 2) | yellowish red |

EXAMPLE 27

2 g aniline in 30 ml alcohol are added dropwise to a solution of 4.5 g 2,9-dichloro-3,8-dimethoxy-N-methoxy-benzo-[c]-cinnolinium methosulphate in 80 ml of water. The mixture is stirred at room temperature for 2 hours and then heated under reflux for 1 hour. When the mixture cools down, a dyestuff is precipitated which dissolves in water with a red colour.

The dyestuff cation of the probable formula

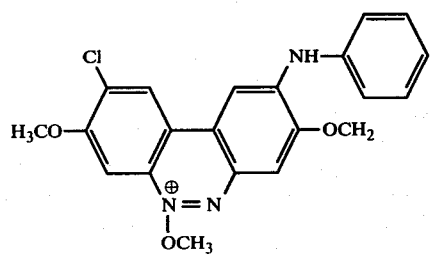

has methosulphate and chloride as anions.

The dyestuff dyes materials of polyacrylonitrile in red shades. It can be converted into the other anions described in Example 1. The dyestuff has the same shades on polyacrylonitrile with these anions.

When the cationic starting compound is replaced in the above Example with equivalent amounts of 2,9-dichloro-3,8-dimethoxy-N-ethoxy-benzo-[c]-cinnolinium ethylsulphate or 2,9-dichloro-3,8-dimethoxy-N-benzyloxy-benzo-[c]-cinnolinium chloride and the condensation is carried out with aniline as described, then dyestuffs are again obtained, which dye materials of polyacrylonitrile in red shades.

When the aniline is replaced in the above Example with equivalent amounts of the amines listed in Column 1 of the following Table, then cationic dyestuffs are likewise obtained, which have the shades specified in Column 2.

| Column 1 Amine | Column 2 Shade on Polyacrylonitrile |
|---|---|
| aniline | red |
| o-toluidine | yellowish red |
| m-toluidine | bluish red |
| 4-chloro-aniline | red |
| p-phenylene-diamine | violet |
| N-acetyl-p-phenylene-diamine | red |
| 4,4-diamino-diphenyl ether | bluish red |
| 4-amino-diphenylamine | black |
| 4-amino-4-methoxy-diphenylamine | " |
| anthranilic acid methyl ester | red |
| 2-methyl-dihydro-(2,3)-indole | violet |
| pyrrolidine | orange-red |
| morpholine | red-orange |
| phenylhydrazine | red |
| o-anisidine | red |
| m-anisidine | " |
| p-anisidine | bluish red |
| benzidine | violet |
| 3-phenyl-pyrazoline-( 2) | red |
| 3-4'-methylphenyl-pyrazoline-( 2) | " |
| 3-4'-ethylphenyl-pyrazoline-( 2) | " |
| 3-3'-methylphenyl-pyrazoline-( 2) | " |
| 3-4'-methylsulphonyl-pyrazoline-( 2) | " |
| 3-4'-methoxyphenyl-pyrazoline-( 2) | " |
| 3-4'-ethoxyphenyl-pyrazoline-( 2) | " |
| 3-4'-n-butoxyphenyl-pyrazoline-( 2) | " |
| 3-4'-iso-amyloxyphenyl-pyrazoline-( 2) | " |
| 3-4'-trifluorophenyl-pyrazoline-( 2) | " |
| 3-4'-fluorophenyl-pyrazoline-( 2) | " |
| 3-4'-chlorophenyl-pyrazoline-( 2) | " |
| 3-4'-bromophenyl-pyrazoline-( 2) | " |
| 3-4'-cyanophenyl-pyrazoline-( 2) | " |
| 3-4'-(β-diethylaminoethoxy)-phenyl-pyrazoline-( 2) | " |
| 3-4'-α-thienyl-pyrazoline-( 2) | " |
| 3-4'-biphenylyl-pyrazoline-( 2) | " |
| 3-3',5'-dimethylphenyl-pyrazoline-( 2) | " |
| 3-3',4'-dimethoxyphenyl-pyrazoline-( 2) | " |
| 3-styryl-5-phenyl-pyrazoline-( 2) | " |
| 3-4'-chlorostyryl-4-4'-chlorophenyl-pyrazoline-( 2) | " |
| 3,4-diphenyl-pyrazoline-( 2) | " |
| 3,5-diphenyl-pyrazoline-( 2) | " |
| 3-phenyl-5,5-dimethyl-pyrazoline-( 2) | " |
| 3-phenyl-4,4-dimethyl-pyrazoline-( 2) | " |

EXAMPLE 28

A fabric of polyacrylonitrile is printed with a printing paste prepared in the following way:

330 parts by weight of hot water are poured over 30 parts by weight of the dyestuff of the probable formula

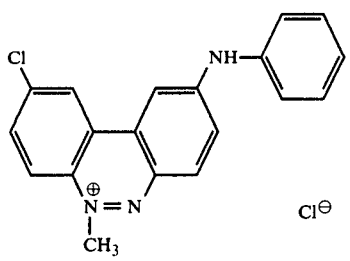

50 parts by weight thiodiethylene glycol, 30 parts by weight cyclohexanol and 30 parts by weight of 30% acetic acid, and the resultant solution is added to 500 parts by weight of crystal gum (gum arabic as thickening agent). 30 Parts by weight of a zinc nitrate solution are finally added. The print obtained is dried, steamed for 30 minutes and subsequently rinsed.

A red print of very good fastness properties is obtained.

EXAMPLE 29

Acid-modified polyglycol terephthalate fibres are introduced in a liquor ratio of 1:40 at 20° C. into an aqueous bath which contains, per liter, 3 to 10 g sodium sulphate, 0.1–1 g oleyl polyglycol ether (50 mol ethylene oxide), 0–15 g dimethyl-benzyl-dodecylammonium chloride and 0.15 g of the dyestuff of the probable formula

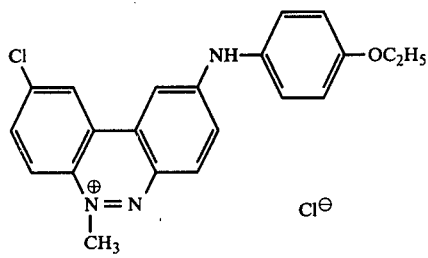

and which has been adjusted to pH 4–5 with acetic acid. The bath is heated to 100° C. in the course of 30 minutes and kept at the same temperature for 60 minutes. The fibres are subsequently rinsed and dried. A Bordeaux dyeing of very good fastness properties is obtained.

EXAMPLE 30

Polyacrylonitrile fibres are introduced in a liquor ratio of 1:40 at 40° C. into an aqueous bath containing, per liter, 0.75 g of 30% acetic acid, 0.38 g sodium acetate and 0.15 g of the dyestuff of the probable formula

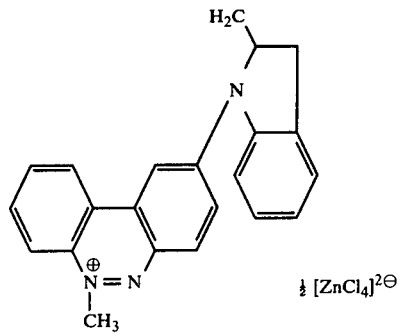

The bath is heated to boiling temperature in the course of 20–30 minutes and kept at the same temperature for 30–60 minutes. After rinsing and drying, a violet dyeing of very good fastness properties is obtained.

EXAMPLE 31

In a dyeing beaker of 500 ml capacity, which is placed on a heated water-bath, 0.055 g of the dyestuff of the probable formula

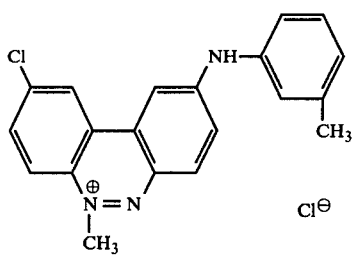

are pasted with 20 times that amount of hot water with the addition of some acetic acid, and then dissolved in hot water. 0.5 g of the reaction product of 50 mol ethylene oxide on 1 mol oleyl alcohol are added to the dyebath which is made up to a volume of 500 ml with cold water. The pH value of the dyebath is adjusted to 4.5 to 5 by means of acetic acid or sodium acetate.

10 g of piece goods of acid-modified polyamide are continuously moved about in this dyebath while the temperature is raised to 100° C. in the course of 15 minutes. The material is dyed at boiling temperature for 15–20 minutes, rinsed with cold water and subsequently dried, for example, by ironing or in a drying cabinet at 60°–70° C.

A red dyeing is obtained.

EXAMPLE 32

Polyacrylonitrile fibres are introduced in a liquor ratio of 1:10 into a perchloroethylene bath containing, per liter, 1 g oleic acid ethanolamide, 1 g of the reaction product of 1 mol oleyl alcohol with 20 mol ethylene oxide, 8 g of water, 1 g of glacial acetic acid, as well as 1 g of the dyestuff of the probable formula

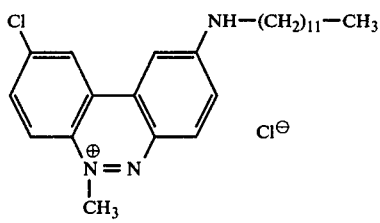

The dyebath is heated in a closed dyeing apparatus at 100° C. for 60 minutes with vigorous agitation of the liquor. The fibres are subsequently rinsed and dried.

An orange dyeing of very good fastness properties is obtained.

EXAMPLE 33

25 Parts of the dyestuff of the probable formula

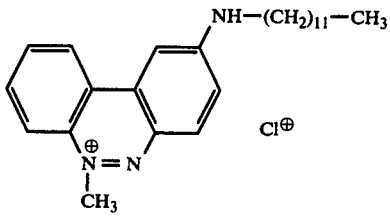

are suspended in 150 parts perchloroethylene, and 65 parts butyrolactone and then 15 parts by weight 2-ethylcaproic acid are added. The dyestuff dissolves with an orange colour. The solution is stirred at 50° C. for a further hour, and suction-filtered after having cooled down again to room temperature. A stable solution is obtained, which is eminently suitable for the dyeing of polyacrylonitrile materials from chlorinated hydrocarbon solutions.

EXAMPLE 34

50 Parts of fibre yarn of anion-modified polyacrylonitrile are introduced at 22° C. into a dyebath consisting of a mixture of 4 parts of the dyestuff solution in perchloroethylene described in Example 33, 4 parts oleic acid ethanolamide, 4parts of the reaction product of 1 mol oleyl alcohol with 20 mol ethylene oxide, 1 part of glacial acetic acid and 8 parts of water in 983 parts perchloroethylene. The bath is heated to 100° C. in the course of 30 minutes with vigorous circulation of the liquor, and kept at the same temperature for one hour.

After this period of time, the liquor is separated and the yarn is freed from any adhering solvent in an air current.

An orange dyeing is obtained.

We claim:

1. Cationic dyestuff of the formula

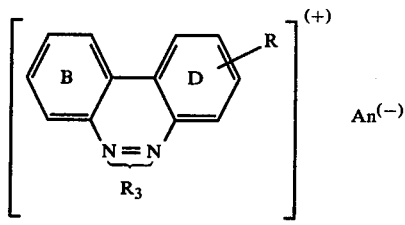

wherein B is unsubstituted or substituted by anilino, methoxy, methyl, cyano, chloro, bromo, nitro, methylamino, tert.-butyl, methoxy-carbonyl, methylcarbonyl, hydroxy, sulphamoyl; except for R, D is unsubstituted or substituted by a member selected from a group consisting of chloro, bromo, methyl, methoxy, nitro and cyano; $An^{(-)}$ is an anion; $R_3$ is methyl, ethyl, n-butyl, iso-amyl, n-propyl, iso-propyl, iso-butyl, 2-methyl-propyl, pentyl, hexyl, cyclohexyl, heptyl, octyl, decyl, dodecyl, benzyl, allyl, ethoxyethyl, ethoxycarbonylmethyl, hydroxyethyl, aminocarbonylethyl, cyanoethyl or NH$_2$; R is anilino, N-methylanilino, N-ethylanilino, N-butylanilino, 2'-chloroanilino, 4'-nitroanilino, 4'-chloro-2' nitroanilino, 2'-methyl-anilino, 6'-chloro-2'-methylanilino 4'-methylanilino, 1-benzylamino, 2',4'-dimethyl-5-nitro-anilino, 2',4',6'-trimethylanilino, 2'-methoxyanilino, 2'-phenoxy-anilino, 2'-acetominoanilino, 2',5'-diethoxyanilino, 3'-cyanoanilino, 4'-methoxycarbonylanilino, 3',4'-dicyanoanilino, 1'-aminonaphthyl, 2'-phenylethylamino, N,N-diphenylamino, methylamino, ethylamino, n-propylamino, isopropylamino, N-n-butylamino, N-cyclohexylamino, N,N-dimethyl-amino, N,N-diethylamino, N-methyl-N-ethylamino, morpholino, piperidino, imidazolyl, 3'-phenyl-pyrazolinyl-(Δ2'), 3'-(4''-methylphenyl)-pyrazolinyl-(Δ2'), 3'-(2''-ethylphenyl)-pyrazolinyl-(Δ2'), 3'-(4''-isopropylphenyl)-pyrazolinyl(Δ2'), 3'-(4''-tert.-butylphenyl)-pyrazolinyl-(Δ2'), 3'-(4''-cyclohexylphenyl)-pyrazolinyl-(Δ2'), 3'-(4''-chlorophenyl)-pyrazolinyl-(Δ2') 3'-(3''-chlorophenyl)-pyrazolinyl-(Δ2'), 3'(2''-chlorophenyl)-pyrazolinyl-(Δ2'), 3'-(2'',4''-dichlorophenyl)-pyrazolinyl-(Δ2'), 3'-(4''-bromo-phenyl)-pyrazolinyl-(Δ2'), 3'-(3'', 4''-dichlorophenyl)-pyrazolinyl-(Δ2'), 3'-(4''-bromophenyl)-pyrazolinyl-(Δ2'), 3'-(4''-fluorophenyl)-pyrazolinyl-(Δ2'), 3'-(4''-difluoro-methyl)-pyrazolinyl-(Δ2'), 3'-(4''-acetylphenyl)-pyrazolinyl-(Δ2'), 3'-(4''-cyanophenyl)-pyrazolinyl-(Δ2'), 3'-(4''-methoxycarbonylphenyl)-pyrazolinyl-(Δ2'), 3'-(4''-methoxyphenyl)-pyrazolinyl-(Δ2'), 3'-(4''-ethoxyphenyl)-pyrazolinyl-(Δ2'), 3'-(4'''-phenoxyphenyl)-pyrazolinyl-(Δ2'), 3'-(4''-isopropoxyphenyl)-pyrazolinyl-(Δ2'), 3'-styryl-5'-phenyl-pyrazolinyl-(Δ2'), 3'-(4''-chlorostyryl)-5'-(4''-chlorophenyl)-pyrazolinyl-(Δ2'), 3'(2'',4''-dichlorophenyl)-pyrazolinyl-(Δ2')-, 3'-2'4''-dichlorostyryl)-5'-(2'',4''-dichlorophenyl)-pyrazolinyl-(Δ2')-, 3'-(2''-thienyl)-pyrazolinyl-(Δ2'), 3'-(5''-methylthienyl-2'')-pyrazolinyl-(Δ2'), 3'-(2''-furyl-pyrazolinyl-(Δ2')-, 3'-[5''-(o,p-dichlorophenyl)-furyl-2'']-pyrazolinyl-(Δ2')-, 3'-(4''-pyridyl)-pyrazolinyl (Δ2'), 3'-(2''-benzoxazolyl)-pyrazolinyl-(Δ2'9, 3'-(2''-benzothiazolyl)-pyrazolinyl-(Δ2'), 3'-(1''-naphthyl)-pyrazolinyl-Δ2'), 3'-(2''-naphthyl)-pyrazolinyl-(Δ2'), 3'-(2''-napthyl)-pyrazolinyl-(Δ2'), 3'-phenyl-4',5'-tetramethylene-pyrazolinyl-(Δ2'), 3', 4'-diphenyl-pyrazolinyl-(Δ2') or 3',5'-diphenyl-pyrazolinyl-(Δ2').

2. Cationic dyestuff of the formula

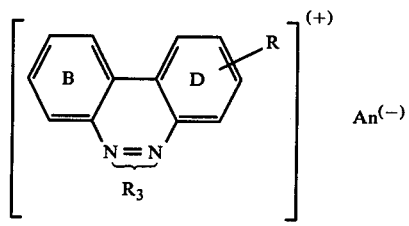

wherein B is unsubstituted or substituted by 8-anilino, 9-anilino, 8-methoxy, 9-methoxy, 8-methyl, 9-methyl, 8-cyano, 9-cyano, 8-chloro, 9-chloro, 8-bromo, 9-bromo, 8,9-dibromo, 8-nitro, 9-nitro, 9-methylamino, 8-tert.-butyl, 9-tert.-butyl, 8-methoxy-carbonyl, 9-methoxycarbonyl, 8-methylcarbonyl, 9-methyl-carbonyl, 8-hydroxy or 8-sulphamoyl; except for R, D is unsubstituted or substituted by a member selected from a group consisting of 3-chloro, 3-bromo, 1-methyl, 3-methyl, 3methoxy, 3-nitro and 3-cyano; $An^{(-)}$ is an anion; $R_3$ is methyl, ethyl, n-butyl, iso-amyl, n-propyl, iso-propyl, iso-butyl, 2-methyl-propyl, pentyl, hexyl, cyclohexyl, heptyl, octyl, decyl, dodecyl, benzyl, allyl, ethoxyethyl, ethoxy-carbonylmethyl, hydroxyethyl, aminocarbonylethyl or cyanoethyl; R is 1-anilino, 2-anilino, 3-anilino, 4-anilino, 2-N-methylanilino, 2-N-ethylanilino, 2-N-butylanilino, 1-[2'-chloroanilino]-, 2-[2'-chloroanilino]-, 2-[4'-nitroanilino], 2-N-methyl-4'-nitro-anilino, 2-[4'-chloro-2'-nitroanilino]-, 2-[2'-methylanilino], 2-[6'-chloro-2'-methylanilino]-, 2-[4'-methylanilino]-, 1-benzylamino-, 2-benzylamino-, 3-benzylamino-, 2-N-benzyl-anilino-, 2-[2',4'-dimethyl-5-nitroanilino]-, [2',4,6'-trimethylanilino]-, 2-[2'methoxyanilino]-, 3-[2'-methoxyanilino-3-[2'-phenoxy-anilino], 2-[2'-acetoaminoanilino], 2-[2',5'-diethoxyanilino, 3-[2',5'-diethoxyanilino], 1-[3'-cyanoanilino], 2-[3'-cyanoanilino], 2-[4'-methoxycarbonylanilino], 2-[3',4'-dicyanoanilino], 3-[3',4'-dicyananilino], 2-[1'-aminonaphthyl], 2-[2'-phenylethylamino], 2-[N,N-diphenylamino 1-methylamino, 2-methylamino, 3-methylamino, 2-ethylamino, 2-n-propyamino, 3-n-propylamino, 2-isopropylamino, 2-N-n-butylamino, 2-N-cyclohexylamino, 1-N,N-dimethylamino, 1-N,N-diethylamino, 2-N,N-diethylamino, 3-N,N-diethylamino, 2-N-methyl-N-ethylamino, 2-morpholino, 2-piperidino, 2-imidazolyl-, 2-[3'-phenylpyrazolinyl-(Δ2')]-, 2-[3'-(4"-methylphenyl)-pyrazolinyl-(Δ2')-, 2-[3'-(2"-ethylphenyl)-pyrazolinyl-(Δ2')]-, 2-[3'-(4"-isopropylphenyl)-pyrazolinyl-(Δ2')-, 2-[3'-(4"-tert.-butylphenyl)-pyrazolinyl-(Δ2')]-, 2-[3'-(4"-cyclohexylphenyl)-pyrazolinyl-(Δ2')]-, 2-[3'-(4"-biphenylyl)-pyrazolinyl-(Δ2')-, 2-[3'-(4"-chlorophenyl)-pyrazolinyl-(Δ2')-, 2-[3'-(3"-chlorophenyl)-pyrazolinyl-(Δ2')]-, 2-[3'-(2"-chlorophenyl)-pyrazolinyl-(Δ2')]-, 2-[3'-(2",4"-dichlorophenyl)-pyrazolinyl-(Δ2')], 2-[3'-("',4"-dichlorophenyl)-pyrazolinyl-(Δ2')-, 2[3'-(4"-bromophenyl)-pyrazolinyl-(Δ2')]-, 2-[3'-(3",4"-dichlorophenyl)-pyrazolinyl-(Δ2')-]-, 2-[3'-(4"-bromophenyl)-pyrazolyinyl (Δ2')], 2-[3-(4"fluorophenyl)-pyrazolinyl-(Δ2')],-, 2-[3'-(4"-difluoromethyl)-pyrazolinyl-(Δ2')]-, 2-[3'-(4"-acetylphenyl)-pyrazolinyl-(Δ2')]-, 2-[3'-(4"-cyanophenyl)-pyrazolinyl-(Δ2')]-, 2-[3'-(4"-methoxycarbonylphenyl)-pyrazolinyl-(Δ2')]-, 2-[3'-(4"-methoxyphenyl)-pyrazolinyl-(Δ2')]-, 2-[3'-(4"-ethoxyphenyl)-pyrazolinyl-(Δ2')]-, 2-[3'-(4"-phenoxyphenyl)-pyrazolinyl-(Δ2')]-, 2-[3'-(4"-isopropoxyphenyl)-pyrazolinyl-(Δ2')], 2-[3'-styryl-5'-phenyl-pyrazolinyl-(66 2')]-, 2-[3'-(4"-chlorostyryl)-5'-(4"-chlorophenyl)-pyrazolinyl-(Δ2')]-, 2-[3'-(2",4"-dichlorophenyl)-pyrazolinyl-(Δ2')]-, 2-[3'-2',4"-dichlorostyryl)-5'-(2",4"-dichlorophenyl)-pyrazolinyl-(Δ2')]-, 2-[3'-(2"-thienyl)-pyrazolinyl-(Δ2']-, 2-[3'-(5"-methylthienyl-2")-pyrazolinyl-(Δ2")]-, 2-[3'-(2"-furyl)-pyrazolinyl-(Δ2')-, 2-]3'-[5"-(o,p,-dichlorophenyl)-furyl-2"/-pyrazolinyl-(Δ2')]-, 2[3'-(4"-pyridyl)-pyrazolinyl-(Δ2')]-, 2-[3'-(2"-benzoxazolyl)-pyrazolinyl-(Δ2')]-, 2-[3'-(2"-benzothiazolyl)-pyrazolinyl-(Δ2')]-, 2[3'-(1"-napthyl)-pyrazolinyl-(Δ2')]-, 2-[3'-(2"-naphthyl)-pyrazolinyl-(Δ2')]-, 2-[3'-phenyl-4',5'-tertamethylene-pyrazolinyl-(Δ2')], 2-[3',4'-diphenyl-pyrazolinyl-(Δ2')]or 2-[3',5'-diphenyl-pyrazolinyl-(Δ2')].

3. Cationic dyestuff of the formula

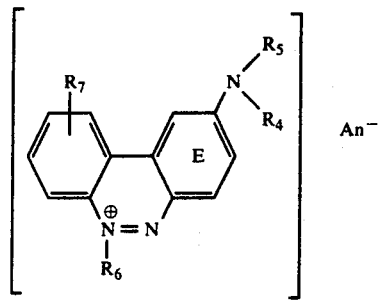

in which $R_4$ means hydrogen, alkyl with 1 to 4 carbon atoms or phenyl; $R_5$ represents hydrogen or alkyl with 1 to 4 carbon atoms; $R_6$ means alkyl with 1 to 3 carbon atoms or benzyl; $R_7$ stands for hydrogen, halogen or alkoxy with 1 to 2 carbon atoms; $An^-$ means the radical of an anion; and in which the ring E may contain 1 or 2 chloro substituents.

4. Cationic dyestuff of claim 3 of the formula

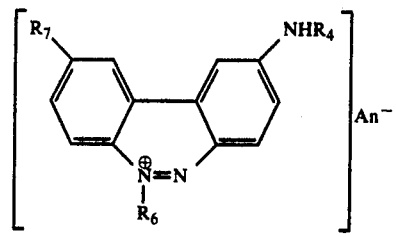

in which $R_4$, $R_6$, $R_7$ and $An^-$ have the same meaning as in claim 4.

5. Cationic dyestuff of the formula

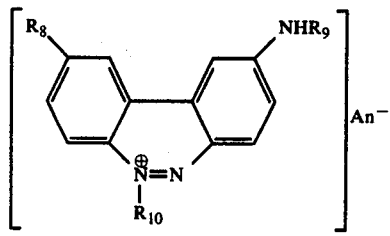

in which $R_8$ stands for Cl, Br, $-OCH_3$, $-OC_2H_5$ or H; $R_9$ stands for $-CH_3$, $-C_2H_5$ or $-C_6H_5$ (phenyl), $-C_6H_4-NH-C_6H_5$, $-C_6H_4-NH-C_6H_4-4-OCH_3$, $-C_6H_4-4-CH_3$, $-C_6H_4-4-OCH_3$ or $-C_6H_4-4-Cl$; $R_{10}$ stands for $-CH_3$, $-C_2H_5$ or $-CH_2C_6H_5$; and $An^-$ means the radical of an anion.

6. A reterocyclic compound of the formula

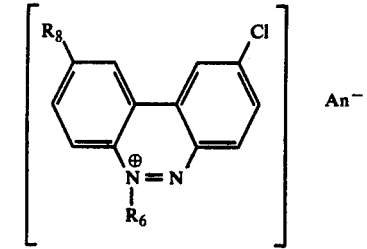

in which $R_8$ stands for H, Cl, Br, $-OCH_3$ or $-OC_2H_5$; $An^-$ means the radical of an anion; and $R_6$ stands for alkyl with 1 to 3 carbon atoms or benzyl.

7. Dyestuff of the formula

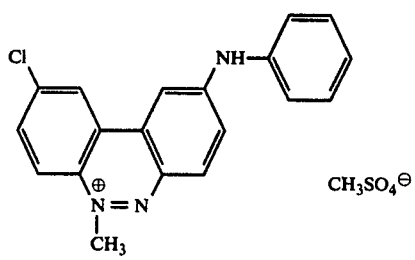

8. Dyestuff of the formula

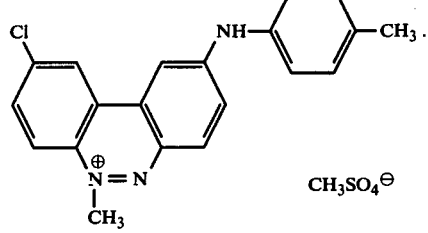
9. Dyestuff of the formula
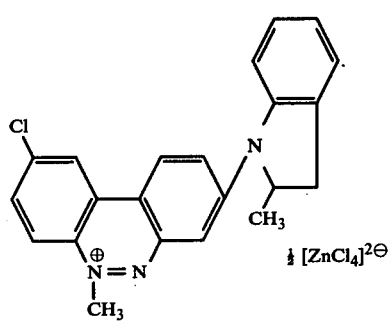
10. Dyestuff of the formula
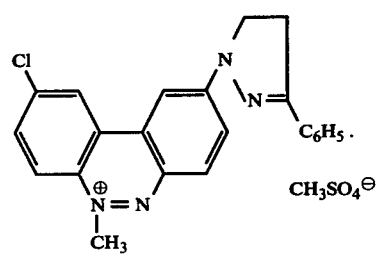
11. Dyestuff of the formula
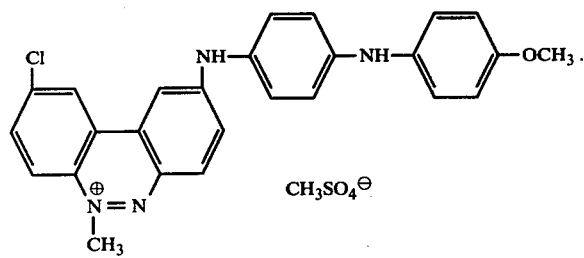
12. Dyestuff of the formula
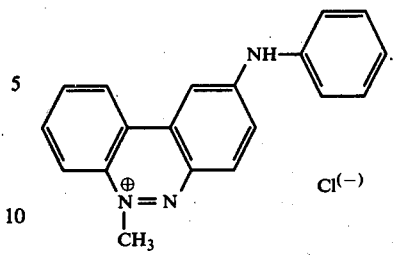
13. Dyestuff of the formula
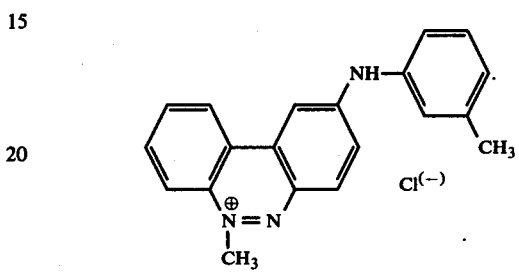
14. Dyestuff of the formula
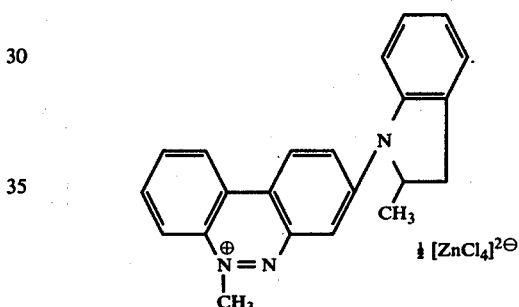
15. Dyestuff of the formula
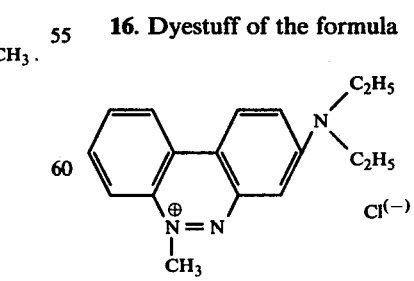
16. Dyestuff of the formula
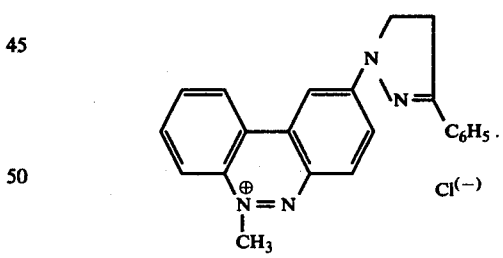
* * * * *